(12) United States Patent
Vess et al.

(10) Patent No.: US 11,992,601 B2
(45) Date of Patent: *May 28, 2024

(54) SYSTEM FOR PROVIDING CONTINUAL DRAINAGE IN NEGATIVE PRESSURE WOUND THERAPY

(71) Applicant: Smith & Nephew, Inc., Memphis, TN (US)

(72) Inventors: Mark A. Vess, Hanson, MA (US); Chirag B. Shah, North Attleboro, MA (US); Richard M. Braga, North Easton, MA (US); David R. Swisher, St. Charles, MO (US)

(73) Assignee: Smith & Nephew, Inc., Memphis, TN (US)

( * ) Notice: Subject to any disclaimer, the term of this patent is extended or adjusted under 35 U.S.C. 154(b) by 795 days.

This patent is subject to a terminal disclaimer.

(21) Appl. No.: 17/087,088

(22) Filed: Nov. 2, 2020

(65) Prior Publication Data

US 2021/0146024 A1 May 20, 2021

Related U.S. Application Data

(60) Continuation of application No. 15/872,810, filed on Jan. 16, 2018, now Pat. No. 10,828,404, which is a
(Continued)

(51) Int. Cl.
*A61M 1/00* (2006.01)
*A61F 13/02* (2006.01)
*A61F 13/00* (2006.01)

(52) U.S. Cl.
CPC .......... *A61M 1/964* (2021.05); *A61F 13/023* (2013.01); *A61M 1/85* (2021.05); *A61M 1/86* (2021.05);
(Continued)

(58) Field of Classification Search
CPC .................. A61F 2013/00174–00178; A61F 2013/00217–00234; A61F 13/02–0243;
(Continued)

(56) References Cited

U.S. PATENT DOCUMENTS 1,585,104 A 5/1926 Montgomery
2,331,271 A 10/1943 Gilchrist
(Continued)

FOREIGN PATENT DOCUMENTS

AU 674837 B2 1/1997
CN 1293953 A 5/2001
(Continued)

OTHER PUBLICATIONS

510K Filing K062227 by KCI USA, Inc. with the Food and Drug Administration on Sep. 27, 2006, 5 pages.
(Continued)

*Primary Examiner* — Susan S Su
(74) *Attorney, Agent, or Firm* — Knobbe, Martens, Olson & Bear, LLP

(57) ABSTRACT

A system for subatmospheric pressure therapy in connection with healing a wound is provided. The system includes a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a vent conduit in fluid communication with the collection canister and the wound
(Continued)

dressing for introducing air into the reservoir to facilitate flow of exudate through the exudate conduit.

20 Claims, 11 Drawing Sheets

Related U.S. Application Data continuation of application No. 14/333,026, filed on Jul. 16, 2014, now Pat. No. 9,889,241, which is a continuation of application No. 13/571,548, filed on Aug. 10, 2012, now Pat. No. 8,784,392, which is a division of application No. 12/475,954, filed on Jun. 1, 2009, now Pat. No. 8,298,200.

(52) U.S. Cl.
CPC ..... *A61M 1/98* (2021.05); *A61F 2013/00089* (2013.01); *A61F 2013/00174* (2013.01); *A61M 1/784* (2021.05); *A61M 1/88* (2021.05); *A61M 2205/7518* (2013.01); *A61M 2205/7536* (2013.01)

(58) Field of Classification Search
CPC .......... A61F 13/023; A61F 2013/00089; A61F 2013/0017; A61M 1/964; A61M 1/85; A61M 1/86; A61M 2205/7518; A61M 2205/7536; A61M 27/00–002
See application file for complete search history.

(56) References Cited

U.S. PATENT DOCUMENTS

| | | |
|---|---|---|
| 2,727,382 A | 12/1955 | Karl et al. |
| 2,736,317 A | 2/1956 | Alexander |
| 2,877,765 A | 3/1959 | John et al. |
| 2,889,039 A | 6/1959 | Peter et al. |
| 3,026,874 A | 3/1962 | Stevens |
| 3,042,041 A | 7/1962 | Jascalevich |
| 3,073,304 A | 1/1963 | Schaar |
| 3,255,749 A | 6/1966 | Smithers |
| 3,285,245 A | 11/1966 | Eldredge et al. |
| 3,367,332 A | 2/1968 | Groves |
| 3,486,504 A | 12/1969 | Austin, Jr. et al. |
| 3,568,675 A | 3/1971 | Harvey |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,880,164 A | 4/1975 | Stepno |
| 3,927,443 A | 12/1975 | Brumlik |
| 3,929,135 A | 12/1975 | Thompson |
| 3,943,734 A | 3/1976 | Fleissner |
| 3,964,039 A | 6/1976 | Craford et al. |
| 3,972,328 A | 8/1976 | Chen |
| 3,980,166 A | 9/1976 | De Feudis |
| 4,029,598 A | 6/1977 | Neisius et al. |
| 4,063,556 A | 12/1977 | Thomas et al. |
| 4,080,970 A | 3/1978 | Miller |
| 4,093,277 A | 6/1978 | Nolan et al. |
| 4,095,599 A | 6/1978 | Simonet-Haibe |
| 4,112,947 A | 9/1978 | Nehring |
| 4,112,949 A | 9/1978 | Rosenthal et al. |
| 4,117,551 A | 9/1978 | Brooks et al. |
| 4,136,696 A | 1/1979 | Nehring |
| 4,164,027 A | 8/1979 | Bonnie et al. |
| 4,169,303 A | 10/1979 | Lemelson |
| 4,202,331 A | 5/1980 | Yale |
| 4,224,941 A | 9/1980 | Stivala |
| 4,224,945 A | 9/1980 | Cohen |
| 4,228,798 A | 10/1980 | Deaton |
| 4,231,357 A | 11/1980 | Hessner |
| 4,261,363 A | 4/1981 | Russo |
| 4,266,545 A | 5/1981 | Moss |
| 4,280,680 A | 7/1981 | Payne |
| 4,360,015 A | 11/1982 | Mayer |
| 4,382,441 A | 5/1983 | Svedman |
| 4,392,853 A | 7/1983 | Muto |
| 4,468,219 A | 8/1984 | George et al. |
| 4,487,606 A | 12/1984 | Leviton et al. |
| 4,499,896 A | 2/1985 | Heinecke |
| 4,508,256 A | 4/1985 | Radel et al. |
| 4,510,802 A | 4/1985 | Peters |
| 4,524,064 A | 6/1985 | Nambu |
| 4,538,645 A | 9/1985 | Perach |
| 4,538,920 A | 9/1985 | Drake |
| 4,540,412 A | 9/1985 | Van Overloop |
| 4,541,426 A | 9/1985 | Webster |
| 4,553,967 A | 11/1985 | Ferguson et al. |
| 4,561,435 A | 12/1985 | McKnight et al. |
| 4,569,674 A | 2/1986 | Phillips et al. |
| 4,579,120 A | 4/1986 | MacGregor |
| 4,600,001 A | 7/1986 | Gilman |
| 4,605,399 A | 8/1986 | Weston et al. |
| 4,614,183 A | 9/1986 | McCracken et al. |
| 4,624,656 A | 11/1986 | Clark et al. |
| 4,655,754 A | 4/1987 | Richmond et al. |
| 4,665,909 A | 5/1987 | Trainor |
| 4,681,562 A | 7/1987 | Beck et al. |
| 4,690,134 A | 9/1987 | Snyders |
| 4,699,134 A | 10/1987 | Samuelsen |
| 4,700,479 A | 10/1987 | Saito et al. |
| 4,710,165 A | 12/1987 | McNeil et al. |
| 4,728,499 A | 3/1988 | Fehder |
| 4,738,257 A | 4/1988 | Meyer et al. |
| 4,743,232 A | 5/1988 | Kruger |
| 4,753,536 A | 6/1988 | Spehar et al. |
| 4,767,026 A | 8/1988 | Keller et al. |
| 4,770,187 A | 9/1988 | Lash et al. |
| 4,771,919 A | 9/1988 | Ernst |
| 4,784,653 A | 11/1988 | Bolton et al. |
| 4,786,282 A | 11/1988 | Wagle et al. |
| 4,807,625 A | 2/1989 | Singleton |
| 4,813,942 A | 3/1989 | Alvarez |
| 4,870,975 A | 10/1989 | Cronk et al. |
| 4,872,450 A | 10/1989 | Austad |
| 4,874,363 A | 10/1989 | Abell |
| 4,886,697 A | 12/1989 | Perdelwitz, Jr. et al. |
| 4,906,240 A | 3/1990 | Reed et al. |
| 4,917,112 A | 4/1990 | Kalt |
| 4,921,492 A | 5/1990 | Schultz et al. |
| 4,941,882 A | 7/1990 | Ward et al. |
| 4,969,880 A | 11/1990 | Zamierowski |
| 4,980,226 A | 12/1990 | Hellgren et al. |
| 4,984,570 A | 1/1991 | Langen et al. |
| 4,985,467 A | 1/1991 | Kelly et al. |
| 4,990,137 A | 2/1991 | Graham |
| 4,995,863 A | 2/1991 | Nichols et al. |
| 4,997,438 A | 3/1991 | Nipper |
| 5,000,172 A | 3/1991 | Ward |
| 5,000,741 A | 3/1991 | Kalt |
| 5,056,510 A | 10/1991 | Gilman |
| 5,059,424 A | 10/1991 | Cartmell et al. |
| 5,060,642 A | 10/1991 | Gilman |
| 5,064,653 A | 11/1991 | Sessions et al. |
| 5,071,409 A | 12/1991 | Rosenberg |
| 5,080,493 A | 1/1992 | McKown et al. |
| 5,080,661 A | 1/1992 | Lavender et al. |
| 5,088,483 A | 2/1992 | Heinecke |
| 5,100,395 A | 3/1992 | Rosenberg |
| 5,100,396 A | 3/1992 | Zamierowski |
| 5,106,362 A | 4/1992 | Gilman |
| 5,106,629 A | 4/1992 | Cartmell et al. |
| 5,112,323 A | 5/1992 | Winkler et al. |
| 5,134,007 A | 7/1992 | Reising et al. |
| 5,135,485 A | 8/1992 | Cohen et al. |
| 5,139,023 A | 8/1992 | Stanley et al. |
| 5,141,503 A | 8/1992 | Sewell, Jr. |
| 5,147,698 A | 9/1992 | Cole |
| 5,149,331 A | 9/1992 | Ferdman et al. |
| 5,152,757 A | 10/1992 | Eriksson |
| 5,160,315 A | 11/1992 | Heinecke et al. |

(56) References Cited

U.S. PATENT DOCUMENTS

| | | |
|---|---|---|
| 5,160,322 A | 11/1992 | Scheremet et al. |
| 5,160,334 A | 11/1992 | Billings et al. |
| 5,176,663 A | 1/1993 | Svedman et al. |
| 5,178,157 A | 1/1993 | Fanlo |
| 5,180,375 A | 1/1993 | Feibus |
| 5,181,905 A | 1/1993 | Flam |
| 5,195,977 A | 3/1993 | Pollitt |
| 5,218,973 A | 6/1993 | Weaver et al. |
| 5,230,496 A | 7/1993 | Shillington et al. |
| 5,238,732 A | 8/1993 | Krishnan |
| 5,244,457 A | 9/1993 | Karami et al. |
| 5,249,709 A | 10/1993 | Duckworth et al. |
| 5,261,893 A | 11/1993 | Zamierowski |
| 5,263,922 A | 11/1993 | Sova et al. |
| 5,264,218 A | 11/1993 | Rogozinski |
| 5,265,605 A | 11/1993 | Afflerbach |
| 5,267,952 A | 12/1993 | Gardner |
| 5,300,054 A | 4/1994 | Feist et al. |
| 5,308,313 A | 5/1994 | Karami et al. |
| 5,333,760 A | 8/1994 | Simmen |
| 5,358,492 A | 10/1994 | Feibus |
| 5,360,420 A | 11/1994 | Cook et al. |
| 5,366,451 A | 11/1994 | Levesque |
| 5,370,610 A | 12/1994 | Reynolds |
| 5,391,161 A | 2/1995 | Hellgren et al. |
| 5,409,472 A | 4/1995 | Rawlings et al. |
| 5,415,627 A | 5/1995 | Rasmussen et al. |
| 5,437,651 A | 8/1995 | Todd et al. |
| 5,439,458 A | 8/1995 | Noel et al. |
| 5,447,492 A | 9/1995 | Cartmell et al. |
| D364,679 S | 11/1995 | Heaton et al. |
| 5,477,492 A | 12/1995 | Ohsaki et al. |
| 5,484,427 A | 1/1996 | Gibbons |
| 5,486,167 A | 1/1996 | Dragoo et al. |
| 5,489,262 A | 2/1996 | Cartmell et al. |
| 5,501,661 A | 3/1996 | Cartmell et al. |
| 5,525,407 A | 6/1996 | Yang |
| 5,527,293 A | 6/1996 | Zamierowski |
| 5,527,923 A | 6/1996 | Klingler et al. |
| 5,531,855 A | 7/1996 | Heinecke et al. |
| 5,536,233 A | 7/1996 | Khouri |
| 5,536,555 A | 7/1996 | Zelazoski et al. |
| 5,549,584 A | 8/1996 | Gross |
| 5,562,107 A | 10/1996 | Lavender et al. |
| 5,582,596 A | 12/1996 | Fukunaga et al. |
| 5,588,958 A | 12/1996 | Cunningham et al. |
| 5,591,149 A | 1/1997 | Cree et al. |
| 5,593,750 A | 1/1997 | Rothrum et al. |
| 5,599,289 A | 2/1997 | Castellana |
| 5,599,333 A | 2/1997 | Atkinson |
| 5,603,145 A | 2/1997 | Arakawa et al. |
| 5,605,165 A | 2/1997 | Sessions et al. |
| 5,609,271 A | 3/1997 | Keller et al. |
| 5,613,942 A | 3/1997 | Lucast et al. |
| 5,618,278 A | 4/1997 | Rothrum |
| 5,624,374 A | 4/1997 | Von Iderstein |
| 5,624,423 A | 4/1997 | Anjur et al. |
| 5,626,954 A | 5/1997 | Andersen et al. |
| 5,636,643 A | 6/1997 | Argenta et al. |
| 5,637,093 A | 6/1997 | Hyman et al. |
| 5,643,189 A | 7/1997 | Masini |
| 5,645,081 A | 7/1997 | Argenta et al. |
| 5,678,564 A | 10/1997 | Lawrence et al. |
| 5,695,846 A | 12/1997 | Lange et al. |
| 5,701,917 A | 12/1997 | Khouri |
| 5,704,905 A | 1/1998 | Jensen et al. |
| 5,707,499 A | 1/1998 | Joshi et al. |
| 5,713,842 A | 2/1998 | Kay |
| 5,733,305 A | 3/1998 | Fleischmann |
| 5,735,145 A | 4/1998 | Pernick |
| 5,735,833 A | 4/1998 | Olson |
| 5,738,656 A | 4/1998 | Wagner |
| 5,749,842 A | 5/1998 | Cheong et al. |
| 5,759,570 A | 6/1998 | Arnold |
| 5,779,657 A | 7/1998 | Daneshvar |
| 5,795,439 A | 8/1998 | Euripides et al. |
| 5,795,584 A | 8/1998 | Totakura et al. |
| 5,797,844 A | 8/1998 | Yoshioka et al. |
| 5,797,894 A | 8/1998 | Cadieux et al. |
| 5,804,021 A | 9/1998 | Abuto et al. |
| 5,833,646 A | 11/1998 | Masini |
| 5,840,049 A | 11/1998 | Tumey et al. |
| 5,840,052 A | 11/1998 | Johns |
| 5,852,126 A | 12/1998 | Barnard et al. |
| 5,868,724 A | 2/1999 | Dierckes, Jr. et al. |
| 5,894,608 A | 4/1999 | Birbara |
| 5,910,150 A | 6/1999 | Saadat |
| 5,911,222 A | 6/1999 | Lawrence et al. |
| 5,914,282 A | 6/1999 | Dunshee et al. |
| 5,928,265 A | 7/1999 | Fleischmann |
| 5,931,800 A | 8/1999 | Rasmussen et al. |
| 5,944,703 A | 8/1999 | Dixon et al. |
| 5,960,795 A | 10/1999 | Schultz |
| 5,960,837 A | 10/1999 | Cude |
| 5,964,723 A | 10/1999 | Augustine |
| 5,968,001 A | 10/1999 | Freeman |
| 5,968,855 A | 10/1999 | Perdelwitz, Jr. et al. |
| 5,973,221 A | 10/1999 | Collyer et al. |
| 6,008,429 A | 12/1999 | Ritger |
| 6,010,524 A | 1/2000 | Fleischmann |
| 6,018,092 A | 1/2000 | Dunshee |
| 6,043,406 A | 3/2000 | Sessions et al. |
| 6,071,267 A | 6/2000 | Zamierowski |
| 6,093,465 A | 7/2000 | Gilchrist et al. |
| 6,117,111 A | 9/2000 | Fleischmann |
| 6,121,508 A | 9/2000 | Bischof et al. |
| 6,129,929 A | 10/2000 | Wick |
| 6,135,116 A | 10/2000 | Vogel et al. |
| D434,150 S | 11/2000 | Tumey et al. |
| 6,142,982 A | 11/2000 | Hunt et al. |
| 6,168,800 B1 | 1/2001 | Dobos et al. |
| 6,174,306 B1 | 1/2001 | Fleischmann |
| 6,203,563 B1 | 3/2001 | Fernandez |
| 6,207,875 B1 | 3/2001 | Lindqvist et al. |
| 6,225,523 B1 | 5/2001 | Masini |
| 6,241,697 B1 | 6/2001 | Augustine |
| 6,252,129 B1 | 6/2001 | Coffee |
| 6,261,276 B1 | 7/2001 | Reitsma |
| 6,261,283 B1 | 7/2001 | Morgan et al. |
| 6,265,605 B1 | 7/2001 | Johnson et al. |
| 6,291,050 B1 | 9/2001 | Cree et al. |
| 6,297,422 B1 | 10/2001 | Hansen et al. |
| 6,312,416 B1 | 11/2001 | Brisebois et al. |
| 6,325,788 B1 | 12/2001 | McKay |
| 6,345,623 B1 | 2/2002 | Heaton et al. |
| 6,348,423 B1 | 2/2002 | Griffiths et al. |
| 6,391,294 B1 | 5/2002 | Dettmar et al. |
| 6,395,955 B1 | 5/2002 | Roe et al. |
| 6,398,761 B1 | 6/2002 | Bills et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,436,432 B2 | 8/2002 | Heinecke et al. |
| 6,447,799 B1 | 9/2002 | Ullman |
| 6,458,109 B1 | 10/2002 | Henley et al. |
| 6,461,467 B2 | 10/2002 | Blatchford et al. |
| 6,478,781 B1 | 11/2002 | Urich et al. |
| 6,479,073 B1 | 11/2002 | Lucast et al. |
| 6,482,491 B1 | 11/2002 | Samuelsen et al. |
| 6,486,285 B2 | 11/2002 | Fujita |
| 6,488,643 B1 | 12/2002 | Tumey et al. |
| 6,497,688 B2 | 12/2002 | Lasko |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| D473,947 S | 4/2003 | Jacobson |
| 6,547,255 B1 | 4/2003 | Donaway et al. |
| 6,553,998 B2 | 4/2003 | Heaton et al. |
| D475,134 S | 5/2003 | Randolph |
| 6,557,704 B1 | 5/2003 | Randolph |
| 6,566,575 B1 | 5/2003 | Stickels et al. |
| 6,599,262 B1 | 7/2003 | Masini |
| D478,659 S | 8/2003 | Hall et al. |

(56) References Cited

U.S. PATENT DOCUMENTS

| | | |
|---|---|---|
| 6,607,495 B1 | 8/2003 | Skalak et al. |
| 6,607,799 B1 | 8/2003 | Heinecke et al. |
| 6,626,891 B2 | 9/2003 | Ohmstede |
| 6,629,774 B1 | 10/2003 | Gruendeman |
| 6,648,862 B2 | 11/2003 | Watson |
| 6,682,506 B1 | 1/2004 | Navarro |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,794,554 B2 | 9/2004 | Sessions et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,878,857 B1 | 4/2005 | Chihani et al. |
| 6,887,228 B2 | 5/2005 | McKay |
| 6,887,263 B2 | 5/2005 | Bleam et al. |
| 6,903,243 B1 | 6/2005 | Burton |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,960,190 B2 | 11/2005 | Stinson |
| 6,979,324 B2 | 12/2005 | Bybordi et al. |
| D515,701 S | 2/2006 | Horhota et al. |
| 6,994,702 B1 | 2/2006 | Johnson |
| 6,994,904 B2 | 2/2006 | Joseph et al. |
| 6,998,511 B2 | 2/2006 | Worthley |
| 7,004,915 B2 | 2/2006 | Boynton et al. |
| 7,005,143 B2 | 2/2006 | Abuelyaman et al. |
| 7,022,113 B2 | 4/2006 | Lockwood et al. |
| 7,037,254 B2 | 5/2006 | O'Connor et al. |
| 7,048,818 B2 | 5/2006 | Krantz et al. |
| 7,052,167 B2 | 5/2006 | Vanderschuit |
| D525,362 S | 7/2006 | Nielsen et al. |
| 7,070,580 B2 | 7/2006 | Nielsen |
| 7,070,584 B2 | 7/2006 | Johnson et al. |
| 7,077,832 B2 | 7/2006 | Fleischmann |
| 7,093,600 B2 | 8/2006 | Sorribes |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,183,454 B1 | 2/2007 | Rosenberg |
| D537,948 S | 3/2007 | Smith |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,267,681 B2 | 9/2007 | Dunshee |
| 7,273,054 B2 | 9/2007 | Heaton et al. |
| 7,276,051 B1 | 10/2007 | Henley et al. |
| 7,276,247 B2 | 10/2007 | Fansler et al. |
| 7,279,612 B1 | 10/2007 | Heaton et al. |
| 7,285,576 B2 | 10/2007 | Hyde et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,381,860 B2 | 6/2008 | Gudnason et al. |
| 7,396,345 B2 | 7/2008 | Knighton et al. |
| 7,401,413 B1 | 7/2008 | Nelson |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,429,689 B2 | 9/2008 | Chen et al. |
| 7,438,705 B2 | 10/2008 | Karpowicz et al. |
| 7,442,849 B2 | 10/2008 | Heinecke |
| 7,468,471 B2 | 12/2008 | Sigurjonsson et al. |
| 7,485,112 B2 | 2/2009 | Karpowicz et al. |
| 7,503,910 B2 | 3/2009 | Adahan |
| 7,524,315 B2 | 4/2009 | Blott et al. |
| 7,531,711 B2 | 5/2009 | Sigurjonsson et al. |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,576,256 B2 | 8/2009 | Bjornberg et al. |
| 7,585,554 B2 | 9/2009 | Johnson et al. |
| 7,586,019 B2 | 9/2009 | Oelund et al. |
| 7,605,298 B2 | 10/2009 | Bechert et al. |
| 7,608,066 B2 | 10/2009 | Vogel |
| 7,611,500 B1 | 11/2009 | Lina et al. |
| 7,612,247 B2 | 11/2009 | Oyaski |
| 7,615,036 B2 | 11/2009 | Joshi et al. |
| 7,622,629 B2 | 11/2009 | Aali |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,674,948 B2 | 3/2010 | Propp et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,723,560 B2 | 5/2010 | Lockwood et al. |
| 7,731,702 B2 | 6/2010 | Bybordi et al. |
| 7,745,681 B1 | 6/2010 | Ferguson |
| 7,749,531 B2 | 7/2010 | Booher |
| 7,754,937 B2 | 7/2010 | Boehringer et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,812,212 B2 | 10/2010 | Propp et al. |
| 7,837,673 B2 | 11/2010 | Vogel |
| 7,846,141 B2 | 12/2010 | Weston |
| 7,857,806 B2 | 12/2010 | Karpowicz et al. |
| 7,862,718 B2 | 1/2011 | Doyen et al. |
| 7,880,050 B2 | 2/2011 | Robinson et al. |
| 7,883,494 B2 | 2/2011 | Martin |
| 7,888,546 B2 | 2/2011 | Marcoux et al. |
| 7,896,823 B2 | 3/2011 | Mangrum et al. |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,927,318 B2 | 4/2011 | Risk, Jr. et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,981,098 B2 | 7/2011 | Boehringer et al. |
| 7,981,136 B2 | 7/2011 | Weiser |
| 7,999,145 B2 | 8/2011 | Kairinos |
| 8,002,313 B2 | 8/2011 | Singh et al. |

(56) References Cited

U.S. PATENT DOCUMENTS

| | | |
|---|---|---|
| 8,021,347 B2 | 9/2011 | Vitaris et al. |
| 8,034,037 B2 | 10/2011 | Adams et al. |
| 8,061,360 B2 | 11/2011 | Locke et al. |
| 8,062,272 B2 | 11/2011 | Weston |
| 8,062,331 B2 | 11/2011 | Zamierowski |
| 8,083,712 B2 | 12/2011 | Biggie et al. |
| 8,097,272 B2 | 1/2012 | Addison |
| 8,100,887 B2 | 1/2012 | Weston et al. |
| 8,105,295 B2 | 1/2012 | Blott et al. |
| 8,128,607 B2 | 3/2012 | Hu et al. |
| 8,133,211 B2 | 3/2012 | Cavanaugh, II et al. |
| 8,147,468 B2 | 4/2012 | Barta et al. |
| 8,148,595 B2 | 4/2012 | Robinson et al. |
| 8,148,596 B2 | 4/2012 | Miau et al. |
| 8,152,785 B2 | 4/2012 | Vitaris |
| 8,158,844 B2 | 4/2012 | McNeil |
| 8,162,907 B2 | 4/2012 | Heagle |
| 8,168,848 B2 | 5/2012 | Lockwood et al. |
| 8,187,237 B2 | 5/2012 | Seegert |
| 8,188,331 B2 | 5/2012 | Barta et al. |
| 8,192,409 B2 | 6/2012 | Hardman et al. |
| 8,197,467 B2 | 6/2012 | Heaton et al. |
| 8,202,261 B2 | 6/2012 | Kazala, Jr. et al. |
| 8,235,939 B2 | 8/2012 | Johnson et al. |
| 8,235,955 B2 | 8/2012 | Blott et al. |
| 8,235,972 B2 | 8/2012 | Adahan |
| 8,241,261 B2 | 8/2012 | Randolph et al. |
| 8,246,606 B2 | 8/2012 | Stevenson et al. |
| 8,257,326 B2 | 9/2012 | Vitaris |
| 8,257,327 B2 | 9/2012 | Blott et al. |
| 8,267,908 B2 | 9/2012 | Coulthard |
| 8,282,611 B2 | 10/2012 | Weston |
| 8,298,200 B2 | 10/2012 | Vess et al. |
| 8,308,703 B2 | 11/2012 | Heaton et al. |
| 8,348,910 B2 | 1/2013 | Blott et al. |
| 8,361,043 B2 | 1/2013 | Hu et al. |
| 8,376,972 B2 | 2/2013 | Fleischmann |
| 8,382,731 B2 | 2/2013 | Johannison |
| 8,404,921 B2 | 3/2013 | Lee et al. |
| 8,430,867 B2 | 4/2013 | Robinson et al. |
| 8,491,548 B2 | 7/2013 | Livne et al. |
| 8,506,554 B2 | 8/2013 | Adahan |
| 8,529,548 B2 | 9/2013 | Blott et al. |
| 8,545,466 B2 | 10/2013 | Andresen et al. |
| 8,608,776 B2 | 12/2013 | Coward et al. |
| 8,617,129 B2 | 12/2013 | Hartwell |
| 8,641,691 B2 | 2/2014 | Fink et al. |
| 8,663,198 B2 | 3/2014 | Buan et al. |
| 8,680,360 B2 | 3/2014 | Greener et al. |
| 8,721,629 B2 | 5/2014 | Hardman et al. |
| 8,734,410 B2 | 5/2014 | Hall et al. |
| 8,784,392 B2 | 7/2014 | Vess et al. |
| 8,801,685 B2 | 8/2014 | Armstrong et al. |
| D714,433 S | 9/2014 | Armstrong et al. |
| 8,843,327 B2 | 9/2014 | Vernon-Harcourt et al. |
| 8,961,481 B2 | 2/2015 | Hu et al. |
| 9,017,302 B2 | 4/2015 | Vitaris et al. |
| 9,033,942 B2 | 5/2015 | Vess |
| D746,435 S | 12/2015 | Armstrong et al. |
| 9,227,000 B2 | 1/2016 | Fink et al. |
| 9,302,032 B2 | 4/2016 | Bannister et al. |
| 9,327,065 B2 | 5/2016 | Albert et al. |
| 9,375,521 B2 | 6/2016 | Hudspeth et al. |
| 9,452,245 B2 | 9/2016 | Jaeb et al. |
| 9,474,654 B2 | 10/2016 | Heagle et al. |
| 9,642,750 B2 | 5/2017 | Albert et al. |
| 9,642,950 B2 | 5/2017 | Hartwell |
| D804,014 S | 11/2017 | Armstrong et al. |
| 9,889,241 B2 | 2/2018 | Vess et al. |
| RE46,825 E | 5/2018 | Heagle |
| 9,956,329 B2 | 5/2018 | Vess |
| 9,974,695 B2 | 5/2018 | Albert et al. |
| 9,999,547 B2 | 6/2018 | Albert et al. |
| 10,016,545 B2 | 7/2018 | Vitaris et al. |
| 10,406,037 B2 | 9/2019 | Albert et al. |
| 10,548,776 B2 | 2/2020 | Greener et al. |
| RE48,117 E | 7/2020 | Albert et al. |
| 10,828,404 B2 | 11/2020 | Vess et al. |
| 11,013,837 B2 | 5/2021 | Blott |
| 11,058,588 B2 | 7/2021 | Albert et al. |
| 11,819,386 B2 | 11/2023 | Brandolini et al. |
| 2001/0020145 A1 | 9/2001 | Satterfield et al. |
| 2001/0031943 A1 | 10/2001 | Urie |
| 2001/0034223 A1 | 10/2001 | Rieser et al. |
| 2001/0043943 A1 | 11/2001 | Coffey |
| 2001/0051165 A1 | 12/2001 | Lenz et al. |
| 2002/0002209 A1 | 1/2002 | Mork |
| 2002/0016577 A1 | 2/2002 | Ohmstede |
| 2002/0035352 A1 | 3/2002 | Ronnberg et al. |
| 2002/0052570 A1 | 5/2002 | Naimer |
| 2002/0062114 A1 | 5/2002 | Murai et al. |
| 2002/0108614 A1 | 8/2002 | Schultz |
| 2002/0143286 A1 | 10/2002 | Tumey |
| 2002/0151836 A1 | 10/2002 | Burden |
| 2002/0182246 A1 | 12/2002 | Oyaski |
| 2003/0014025 A1 | 1/2003 | Allen et al. |
| 2003/0014786 P1 | 1/2003 | Meilland |
| 2003/0078532 A1 | 4/2003 | Ruszczak et al. |
| 2003/0093041 A1 | 5/2003 | Risk, Jr. et al. |
| 2003/0125646 A1 | 7/2003 | Whitlock |
| 2003/0181850 A1 | 9/2003 | Diamond et al. |
| 2003/0212357 A1 | 11/2003 | Pace |
| 2003/0212359 A1 | 11/2003 | Butler |
| 2003/0219469 A1 | 11/2003 | Johnson et al. |
| 2003/0225347 A1 | 12/2003 | Argenta et al. |
| 2004/0015115 A1 | 1/2004 | Sinyagin |
| 2004/0019338 A1 | 1/2004 | Litvay et al. |
| 2004/0039415 A1 | 2/2004 | Zamierowski |
| 2004/0057855 A1 | 3/2004 | Gerlach et al. |
| 2004/0064111 A1 | 4/2004 | Lockwood et al. |
| 2004/0064132 A1 | 4/2004 | Boehringer et al. |
| 2004/0087884 A1 | 5/2004 | Haddock et al. |
| 2004/0093026 A1 | 5/2004 | Weidenhagen et al. |
| 2004/0113309 A1 | 6/2004 | Thompson et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0249353 A1 | 12/2004 | Risks, Jr. et al. |
| 2004/0260230 A1 | 12/2004 | Randolph |
| 2005/0004234 A1 | 1/2005 | Bell et al. |
| 2005/0004501 A1 | 1/2005 | Lorenzo |
| 2005/0020955 A1 | 1/2005 | Sanders et al. |
| 2005/0065484 A1 | 3/2005 | Watson, Jr. |
| 2005/0084641 A1 | 4/2005 | Downs et al. |
| 2005/0085795 A1 | 4/2005 | Lockwood et al. |
| 2005/0090787 A1 | 4/2005 | Risk, Jr. et al. |
| 2005/0090860 A1 | 4/2005 | Paprocki |
| 2005/0101940 A1 | 5/2005 | Radl et al. |
| 2005/0107756 A1 | 5/2005 | McCraw |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0147656 A1 | 7/2005 | McCarthy et al. |
| 2005/0177190 A1 | 8/2005 | Zamierowski |
| 2005/0182445 A1 | 8/2005 | Zamierowski |
| 2005/0273066 A1 | 12/2005 | Wittmann |
| 2005/0288691 A1 | 12/2005 | Leiboff |
| 2006/0009744 A1 | 1/2006 | Erdman et al. |
| 2006/0020234 A1 | 1/2006 | Chou et al. |
| 2006/0029650 A1 | 2/2006 | Coffey |
| 2006/0036221 A1 | 2/2006 | Watson, Jr. |
| 2006/0039742 A1 | 2/2006 | Cable, Jr. et al. |
| 2006/0047257 A1 | 3/2006 | Raidel et al. |
| 2006/0100586 A1 | 5/2006 | Karpowicz et al. |
| 2006/0149170 A1 | 7/2006 | Boynton et al. |
| 2006/0184150 A1 | 8/2006 | Noel |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz et al. |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |

(56) References Cited

U.S. PATENT DOCUMENTS

| | | |
|---|---|---|
| 2007/0032778 A1 | 2/2007 | Heaton et al. |
| 2007/0040454 A1 | 2/2007 | Freudenberger et al. |
| 2007/0055209 A1 | 3/2007 | Patel et al. |
| 2007/0060892 A1 | 3/2007 | Propp |
| 2007/0078432 A1 | 4/2007 | Halseth et al. |
| 2007/0178145 A1 | 8/2007 | Chou et al. |
| 2007/0179460 A1 | 8/2007 | Adahan |
| 2007/0185463 A1 | 8/2007 | Mulligan |
| 2007/0219513 A1 | 9/2007 | Lina et al. |
| 2007/0219532 A1* | 9/2007 | Karpowicz ............ A61M 1/96 604/540 |
| 2007/0220692 A1 | 9/2007 | Kusin |
| 2007/0225663 A1 | 9/2007 | Watt et al. |
| 2007/0233022 A1 | 10/2007 | Henley et al. |
| 2007/0239232 A1 | 10/2007 | Kurtz et al. |
| 2007/0265561 A1 | 11/2007 | Yeung |
| 2007/0282310 A1 | 12/2007 | Bengtson et al. |
| 2008/0011667 A1 | 1/2008 | Ruschke |
| 2008/0031748 A1 | 2/2008 | Ihle et al. |
| 2008/0051688 A1 | 2/2008 | Lowe |
| 2008/0071235 A1 | 3/2008 | Locke et al. |
| 2008/0082084 A1 | 4/2008 | Roberts et al. |
| 2008/0103462 A1 | 5/2008 | Wenzel et al. |
| 2008/0103489 A1 | 5/2008 | Dahners |
| 2008/0108977 A1 | 5/2008 | Heaton et al. |
| 2008/0113143 A1 | 5/2008 | Taylor |
| 2008/0132819 A1 | 6/2008 | Radl et al. |
| 2008/0161778 A1 | 7/2008 | Steward |
| 2008/0167593 A1 | 7/2008 | Fleischmann |
| 2008/0172017 A1 | 7/2008 | Carlucci et al. |
| 2008/0183233 A1 | 7/2008 | Koch et al. |
| 2008/0200096 A1 | 8/2008 | Thornton et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0215019 A1 | 9/2008 | Malamutmann |
| 2008/0234641 A1 | 9/2008 | Locke et al. |
| 2008/0281281 A1 | 11/2008 | Meyer et al. |
| 2008/0287892 A1 | 11/2008 | Khan et al. |
| 2008/0300578 A1 | 12/2008 | Freedman |
| 2008/0306456 A1 | 12/2008 | Riesinger |
| 2008/0312572 A1 | 12/2008 | Riesinger |
| 2009/0099519 A1 | 4/2009 | Kaplan |
| 2009/0105670 A1 | 4/2009 | Bentley et al. |
| 2009/0125004 A1 | 5/2009 | Shen et al. |
| 2009/0131892 A1 | 5/2009 | Karpowicz et al. |
| 2009/0157016 A1 | 6/2009 | Adahan |
| 2009/0157024 A1 | 6/2009 | Song |
| 2009/0171288 A1 | 7/2009 | Wheeler |
| 2009/0234306 A1 | 9/2009 | Vitaris |
| 2009/0234313 A1 | 9/2009 | Mullejeans et al. |
| 2009/0264805 A1 | 10/2009 | Davis et al. |
| 2009/0281526 A1 | 11/2009 | Kenny et al. |
| 2009/0287133 A1 | 11/2009 | LaGreca, Sr. |
| 2009/0293887 A1 | 12/2009 | Wilkes et al. |
| 2009/0299249 A1 | 12/2009 | Wilkes et al. |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0299308 A1 | 12/2009 | Kazala, Jr. et al. |
| 2009/0299340 A1 | 12/2009 | Kazala, Jr. et al. |
| 2009/0326430 A1 | 12/2009 | Frederiksen et al. |
| 2010/0000524 A1 | 1/2010 | Ohbi |
| 2010/0010458 A1 | 1/2010 | Sherman |
| 2010/0028390 A1 | 2/2010 | Cleary et al. |
| 2010/0057025 A1 | 3/2010 | Aicher |
| 2010/0063484 A1 | 3/2010 | Heagle |
| 2010/0069850 A1 | 3/2010 | Fabo |
| 2010/0069858 A1 | 3/2010 | Olson |
| 2010/0069863 A1 | 3/2010 | Olson |
| 2010/0106106 A1 | 4/2010 | Heaton et al. |
| 2010/0106108 A1 | 4/2010 | Hirsch |
| 2010/0106114 A1 | 4/2010 | Weston et al. |
| 2010/0106121 A1 | 4/2010 | Holm |
| 2010/0106188 A1 | 4/2010 | Heaton et al. |
| 2010/0125258 A1 | 5/2010 | Coulthard et al. |
| 2010/0137775 A1 | 6/2010 | Hu et al. |
| 2010/0160901 A1 | 6/2010 | Hu et al. |
| 2010/0191197 A1 | 7/2010 | Braga et al. |
| 2010/0191198 A1 | 7/2010 | Heagle |
| 2010/0210986 A1 | 8/2010 | Sanders et al. |
| 2010/0259406 A1 | 10/2010 | Caso et al. |
| 2010/0262091 A1 | 10/2010 | Larsson |
| 2010/0262094 A1 | 10/2010 | Walton et al. |
| 2010/0268128 A1 | 10/2010 | Randolph |
| 2010/0286638 A1 | 11/2010 | Malhi |
| 2010/0312159 A1 | 12/2010 | Aali et al. |
| 2011/0021964 A1 | 1/2011 | Larsen et al. |
| 2011/0028919 A1 | 2/2011 | Johnnison et al. |
| 2011/0054421 A1 | 3/2011 | Hartwell |
| 2011/0070391 A1 | 3/2011 | Cotton |
| 2011/0118683 A1 | 5/2011 | Weston |
| 2011/0125110 A1 | 5/2011 | Cotton |
| 2011/0130712 A1 | 6/2011 | Topaz |
| 2011/0213320 A1 | 9/2011 | Blott et al. |
| 2011/0313373 A1 | 12/2011 | Riesinger |
| 2012/0116334 A1 | 5/2012 | Albert et al. |
| 2012/0302976 A1 | 11/2012 | Locke et al. |
| 2013/0226115 A1 | 8/2013 | Robinson et al. |
| 2013/0226152 A1 | 8/2013 | Zolli |
| 2015/0018785 A1 | 1/2015 | Vess et al. |
| 2018/0369462 A1 | 12/2018 | Anderson et al. |
| 2019/0343994 A1 | 11/2019 | Greener |
| 2020/0100945 A1 | 4/2020 | Albert et al. |
| 2023/0043747 A1 | 2/2023 | Albert et al. |
| 2023/0103651 A1 | 4/2023 | Anderson et al. |
| 2023/0181375 A1 | 6/2023 | Albert et al. |
| 2023/0338638 A1 | 10/2023 | Johnson et al. |

FOREIGN PATENT DOCUMENTS

| | | |
|---|---|---|
| CN | 2676918 Y | 2/2005 |
| CN | 2843399 Y | 12/2006 |
| CN | 201139694 Y | 10/2008 |
| CN | 101415818 A | 4/2009 |
| DE | 3443101 A1 | 5/1986 |
| DE | 3907007 A1 | 9/1990 |
| DE | 4030465 A1 | 4/1992 |
| DE | 4111122 A1 | 4/1993 |
| DE | 4306478 A1 | 9/1994 |
| DE | 29504378 U1 | 9/1995 |
| DE | 19844355 A1 | 4/2000 |
| EP | 0053936 A2 | 6/1982 |
| EP | 0340018 A2 | 11/1989 |
| EP | 0358302 A2 | 3/1990 |
| EP | 0325771 B1 | 9/1993 |
| EP | 0392640 B1 | 6/1995 |
| EP | 0441418 B1 | 7/1995 |
| EP | 0751757 A1 | 1/1997 |
| EP | 0853950 A1 | 7/1998 |
| EP | 0651983 B1 | 9/1998 |
| EP | 0777504 B1 | 10/1998 |
| EP | 0774242 B1 | 3/2000 |
| EP | 1018967 A1 | 7/2000 |
| EP | 1088569 A2 | 4/2001 |
| EP | 0674892 B1 | 7/2001 |
| EP | 0921775 B1 | 12/2001 |
| EP | 1169071 A1 | 1/2002 |
| EP | 0948951 B1 | 6/2002 |
| EP | 1219311 A2 | 7/2002 |
| EP | 1283702 A1 | 2/2003 |
| EP | 0729334 B1 | 3/2003 |
| EP | 1353001 A1 | 10/2003 |
| EP | 1440667 A1 | 7/2004 |
| EP | 1487389 A1 | 12/2004 |
| EP | 1556120 A2 | 7/2005 |
| EP | 0982015 B1 | 8/2006 |
| EP | 1955887 A2 | 8/2008 |
| EP | 1620720 B1 | 10/2008 |
| EP | 1977776 A2 | 10/2008 |
| EP | 2010065 A1 | 1/2009 |
| EP | 2138139 A2 | 12/2009 |
| EP | 1652549 B1 | 1/2010 |
| EP | 1905465 B1 | 1/2010 |

(56) References Cited

FOREIGN PATENT DOCUMENTS

| | | | |
|---|---|---|---|
| EP | 1314410 B1 | 2/2010 |
| EP | 2152196 A1 | 2/2010 |
| EP | 2203137 A1 | 7/2010 |
| EP | 2218431 A2 | 8/2010 |
| EP | 2244217 A1 | 10/2010 |
| EP | 2244746 A2 | 11/2010 |
| EP | 2319550 A1 | 5/2011 |
| EP | 1578477 B1 | 9/2011 |
| EP | 2413858 A1 | 2/2012 |
| EP | 2529766 A3 | 12/2012 |
| EP | 2545946 A3 | 3/2013 |
| EP | 1906903 B1 | 4/2014 |
| EP | 2628500 B1 | 5/2014 |
| EP | 1339366 B1 | 6/2014 |
| EP | 2051675 B1 | 6/2014 |
| EP | 2285430 B1 | 8/2014 |
| EP | 2269603 B1 | 5/2015 |
| EP | 2437802 B1 | 5/2016 |
| FR | 1163907 A | 10/1958 |
| GB | 488232 A | 7/1938 |
| GB | 1220857 A | 1/1971 |
| GB | 1255395 A | 12/1971 |
| GB | 1415096 A | 11/1975 |
| GB | 1549756 A | 8/1979 |
| GB | 2195255 A | 4/1988 |
| GB | 2235877 A | 3/1991 |
| GB | 2307180 A | 5/1997 |
| GB | 2329127 A | 3/1999 |
| GB | 2331937 A | 6/1999 |
| GB | 2336546 A | 10/1999 |
| GB | 2307180 B | 6/2000 |
| GB | 2336546 B | 6/2000 |
| GB | 2344531 A | 6/2000 |
| GB | 2389794 A | 12/2003 |
| GB | 2415908 A | 1/2006 |
| GB | 2431351 A | 4/2007 |
| GB | 2468905 A | 9/2010 |
| JP | S5230463 U | 3/1977 |
| JP | H02131432 U | 11/1990 |
| JP | H04503625 A | 7/1992 |
| JP | 2001314479 A | 11/2001 |
| JP | 2006025918 A | 2/2006 |
| JP | 2008073187 A | 4/2008 |
| JP | 2008183244 A | 8/2008 |
| RU | 62504 U1 | 4/2007 |
| SU | 1762940 A1 | 9/1992 |
| WO | WO-8001139 A1 | 6/1980 |
| WO | WO-8002182 A1 | 10/1980 |
| WO | WO-8300742 A1 | 3/1983 |
| WO | WO-8401904 A1 | 5/1984 |
| WO | WO-8905133 A1 | 6/1989 |
| WO | WO-9011795 A1 | 10/1990 |
| WO | WO-9216245 A1 | 10/1992 |
| WO | WO-9219313 A1 | 11/1992 |
| WO | WO-9309727 A1 | 5/1993 |
| WO | WO-9420041 A1 | 9/1994 |
| WO | WO-9421207 A2 | 9/1994 |
| WO | WO-9423678 A1 | 10/1994 |
| WO | WO-9605873 A1 | 2/1996 |
| WO | WO-9741816 A1 | 11/1997 |
| WO | WO-9963922 A1 | 12/1999 |
| WO | WO-0021586 A1 | 4/2000 |
| WO | WO-0154743 A1 | 8/2001 |
| WO | WO-0185228 A2 | 11/2001 |
| WO | WO-02070040 A1 | 9/2002 |
| WO | WO-02092783 A2 | 11/2002 |
| WO | WO-03005943 A2 | 1/2003 |
| WO | WO-03018098 A2 | 3/2003 |
| WO | WO-03030966 A1 | 4/2003 |
| WO | WO-03045492 A1 | 6/2003 |
| WO | WO-03051409 A1 | 6/2003 |
| WO | WO-03057070 A2 | 7/2003 |
| WO | WO-03057071 A2 | 7/2003 |
| WO | WO-03057307 A1 | 7/2003 |
| WO | WO-03086232 A2 | 10/2003 |
| WO | WO-03092620 A2 | 11/2003 |
| WO | WO-03101508 A2 | 12/2003 |
| WO | WO-2004018020 A1 | 3/2004 |
| WO | WO-2004041064 A2 | 5/2004 |
| WO | WO-2004077387 A1 | 9/2004 |
| WO | WO-2005009488 A2 | 2/2005 |
| WO | WO-2005016179 A2 | 2/2005 |
| WO | WO-2005061025 A1 | 7/2005 |
| WO | WO-2005072789 A2 | 8/2005 |
| WO | WO-2005105174 A1 | 11/2005 |
| WO | WO-2005105175 A1 | 11/2005 |
| WO | WO-2005105176 A1 | 11/2005 |
| WO | WO-2005105180 A1 | 11/2005 |
| WO | WO-2005107842 A1 | 11/2005 |
| WO | WO-2005115523 A1 | 12/2005 |
| WO | WO-2006015599 A1 | 2/2006 |
| WO | WO-2006105892 A1 | 10/2006 |
| WO | WO-2006114638 A2 | 11/2006 |
| WO | WO-2006114648 A2 | 11/2006 |
| WO | WO-2007006306 A2 | 1/2007 |
| WO | WO-2007013064 A1 | 2/2007 |
| WO | WO-2007016590 A2 | 2/2007 |
| WO | WO-2007019038 A2 | 2/2007 |
| WO | WO-2007031757 A1 | 3/2007 |
| WO | WO-2007031762 A1 | 3/2007 |
| WO | WO-2007031765 A1 | 3/2007 |
| WO | WO-2007041642 A2 | 4/2007 |
| WO | WO-2007062024 A1 | 5/2007 |
| WO | WO-2007066699 A1 | 6/2007 |
| WO | WO-2007067685 A2 | 6/2007 |
| WO | WO-2007084792 A2 | 7/2007 |
| WO | WO-2007085396 A1 | 8/2007 |
| WO | WO-2007087808 A1 | 8/2007 |
| WO | WO-2007087809 A1 | 8/2007 |
| WO | WO-2007087811 A1 | 8/2007 |
| WO | WO-2007092397 A2 | 8/2007 |
| WO | WO-2007095180 A2 | 8/2007 |
| WO | WO-2007106590 A2 | 9/2007 |
| WO | WO-2007106591 A2 | 9/2007 |
| WO | WO-2007106592 A2 | 9/2007 |
| WO | WO-2007113597 A2 | 10/2007 |
| WO | WO-2007143060 A2 | 12/2007 |
| WO | WO-2008008032 A1 | 1/2008 |
| WO | WO-2008010094 A2 | 1/2008 |
| WO | WO-2008011774 A1 | 1/2008 |
| WO | WO-2008012278 A1 | 1/2008 |
| WO | WO-2008020862 A1 | 2/2008 |
| WO | WO-2008027449 A2 | 3/2008 |
| WO | WO-2008040020 A2 | 4/2008 |
| WO | WO-2008043067 A2 | 4/2008 |
| WO | WO-2008048481 A2 | 4/2008 |
| WO | WO-2008100440 A1 | 8/2008 |
| WO | WO-2008100446 A2 | 8/2008 |
| WO | WO-2008112304 A1 | 9/2008 |
| WO | WO-2008131895 A1 | 11/2008 |
| WO | WO-2008132215 A1 | 11/2008 |
| WO | WO-2008135997 A2 | 11/2008 |
| WO | WO-2008141470 A1 | 11/2008 |
| WO | WO-2008154158 A2 | 12/2008 |
| WO | WO-2009001590 A1 | 12/2008 |
| WO | WO-2009004370 A1 | 1/2009 |
| WO | WO-2009016603 A2 | 2/2009 |
| WO | WO-2009016605 A2 | 2/2009 |
| WO | WO-2009019229 A2 | 2/2009 |
| WO | WO-2009021047 A2 | 2/2009 |
| WO | WO-2009021353 A1 | 2/2009 |
| WO | WO-2009021523 A1 | 2/2009 |
| WO | WO-2009034322 A2 | 3/2009 |
| WO | WO-2009066104 A1 | 5/2009 |
| WO | WO-2009066106 A1 | 5/2009 |
| WO | WO-2009068665 A1 | 6/2009 |
| WO | WO-2009071929 A2 | 6/2009 |
| WO | WO-2009071932 A2 | 6/2009 |
| WO | WO-2009071935 A1 | 6/2009 |
| WO | WO-2009071948 A1 | 6/2009 |
| WO | WO-2009078790 A1 | 6/2009 |
| WO | WO-2009086580 A1 | 7/2009 |
| WO | WO-2009088925 A1 | 7/2009 |
| WO | WO-2009111655 A2 | 9/2009 |

(56) References Cited

FOREIGN PATENT DOCUMENTS

| | | |
|---|---|---|
| WO | WO-2009114624 A2 | 9/2009 |
| WO | WO-2009114760 A1 | 9/2009 |
| WO | WO-2009114786 A2 | 9/2009 |
| WO | WO-2009124100 A1 | 10/2009 |
| WO | WO-2009124473 A1 | 10/2009 |
| WO | WO-2009124548 A1 | 10/2009 |
| WO | WO-2009135171 A2 | 11/2009 |
| WO | WO-2009137194 A2 | 11/2009 |
| WO | WO-2009140376 A1 | 11/2009 |
| WO | WO-2009141820 A1 | 11/2009 |
| WO | WO-2009145703 A1 | 12/2009 |
| WO | WO-2009145894 A1 | 12/2009 |
| WO | WO-2009147402 A2 | 12/2009 |
| WO | WO-2009156949 A2 | 12/2009 |
| WO | WO-2010014177 A2 | 2/2010 |
| WO | WO-2010033769 A1 | 3/2010 |
| WO | WO-2010035017 A1 | 4/2010 |
| WO | WO-2010042240 A1 | 4/2010 |
| WO | WO-2010051073 A1 | 5/2010 |
| WO | WO-2010059730 A2 | 5/2010 |
| WO | WO-2010072395 A1 | 7/2010 |
| WO | WO-2010078166 A2 | 7/2010 |
| WO | WO-2010147533 A1 | 12/2010 |
| WO | WO-2011049562 A1 | 4/2011 |
| WO | WO-2011100851 A1 | 8/2011 |
| WO | WO-2011115908 A1 | 9/2011 |
| WO | WO-2012142002 A1 | 10/2012 |
| WO | WO-2012166428 A1 | 12/2012 |
| WO | WO-2012174672 A1 | 12/2012 |
| WO | WO-2013013938 A1 | 1/2013 |
| WO | WO-2013016239 A1 | 1/2013 |
| WO | WO-2013019438 A1 | 2/2013 |
| WO | WO-2013043972 A1 | 3/2013 |
| WO | WO-2013123005 A1 | 8/2013 |
| WO | WO-2014066057 A1 | 5/2014 |
| WO | WO-2014043238 A3 | 9/2014 |
| WO | WO-2014158526 A1 | 10/2014 |

OTHER PUBLICATIONS

Bevan D., et al., "Diverse and potent activities of HGF/SF in skin wound repair," Journal of Pathology, vol. 203, 2004, pp. 831-838.
Expert Declaration by Carianne Nilsson for Post Grant Review of U.S. Pat. No. 9,642,750, dated Feb. 8, 2018, 13 pages.
Expert Declaration by Dr. Michael Helmus for Post Grant Review of U.S. Pat. No. 9,642,750, dated Feb. 9, 2018, 184 pages.
Info V.A.C. User Manual, KCI on Dec. 1, 2006 in 76 pages.
"KCI—The Clinical Advantage", Presentation by KCI with English translation, 61 pages. (publication date unknown).
Landis E.M., et al., "The Effects of Alternate Suction and Pressure on Blood Flow to the Lower Extremities," Alternate Suction and Pressure, J Clin Invest, Sep. 1993, vol. 12 (5), pp. 925-961.
Mitchell R.N., et al., "Role of Stem Cells in Tissue Homeostasis," Pocket Companion to Robbins and Cotran Pathologic Basis of Disease, 7th Edition, 2006, p. 55 (3 pages).
Morykwas M.J., et al., "Nonsurgical Modalities to Enhance Healing and Care of Soft Tissue Wounds," Journal of the Southern Orthopaedic Association, vol. 6, No. 4, 1997, pp. 279-288.
Petition for Post-Grant Review of U.S. Pat. No. 9,642,750 dated Feb. 9, 2018 in 2271 pages filed by Molnlycke Health Care AB, including the following Exhibits: U.S. Pat. No. 9,642,750; Prosecution history of U.S. Pat. No. 9,642,750; U.S. Pat. No. 9,327,065; U.S. Pat. No. 8,801,685; U.S. Appl. No. 61/369,008; U.S. Appl. No. 61/332,440; U.S. Appl. No. 61/289,358; U.S. Pat. Pub. No. 2015/0359951; Prosecution history of U.S. Appl. No. 14/761,335; Expert Declaration by Dr. Michael Helmus; Expert Declaration by Carianne Nilsson; U.S. Pat. Pub. No. 2010/0137775; U.S. Pat. Pub. No. 2009/0227968; U.S. Pat. Pub. No. 2010/0106108; U.S. Appl. No. 61/109,360; http://www.merriam-webster.com/dictionary/obstruct, accessed Feb. 2, 2018; http://www.merriam-webster.com/dictionary/obstruct, accessed Feb. 2, 2018; http://www.merriam-webster.com/dictionary/obstruct, accessed Feb. 2, 2018; http://www.merriam-webster.com/dictionary/obstruct, accessed Feb. 2, 2018; KCI user's manual, Dec. 2006; Trademark prosecution history for SENSAT.R. A.C.; Presentation from KCI; Certified English translation of "Presentation from KCI"; Certification of translation of "Presentation from KCI"; "KCI Launches Next Generation Wound Care TherapySystems" (http://www.merriam-webster.com/dictionary/obstruct) Aug. 30, 2007; KCI product catalog, 2009; KCI user's manual, Mar. 5, 2010; 510K filing K062227 by KCI with the Food and Drug Administration on Sep. 27, 2006; 510K filing K022011 by KCI with the Food and Drug Administration on Jun. 19, 2002; Images of SensaTRAC produced in 2016.
"SensaT.R.A.C.™ Technology—An Essential Component of V.A. C.® Therapy", KCI user's manual, Mar. 5, 2010, 2 pages.
Smith and Nephew Inc., "Allevyn Wound Dressings Pamphlet," 2008, 2 pages.
Trademark Prosecution History for SENSAT.R.A.C, specifying a date of first use of Jun. 14, 2007, 112 pages.
"V.A.C. Freedom® and V.A.C. ATS® Therapy Systems—Active Healing by Designs", KCI product catalog, 2009, LIT 29-A-194, 4 pages.
Annex to the Communication, the Opposition of European Patent No. 2437802, dated Oct. 6, 2017, 13 pages.
Arnljots B., et al., "Irrigation Treatment in Split-Thickness Skin Grafting of Intractable Leg Ulcers," Scandinavian Journal of Plastic and Reconstructive Surgery, vol. 19, 1985, pp. 211-213.
Aubrey D.A., et al., "Treatment of the Perineal Wound after Proctectomy by Intermittent Irrigation," Arch. Surg, vol. 119, Oct. 1984, pp. 1141-1144.
Bagautdinov N.A., "Variant of External Vacuum Aspiration in the Treatment of Purulent Diseases of Soft Tissues," in Current Problems in Modern Clinical Surgery, Interdepartmental Collection, 1986, pp. 94-96.
Bier A., "Hyperemia as a Therapeutic Agent," UCI CCM Library, 1905, pp. 74-85.
Boehringer Wound Systems, LLC, "Engenex™," Instructions for Use, Aug. 2007, pp. 1-33.
Bucalo B., et al., "Inhibition of Cell Proliferation by Chronic Wound Fluid," Wound Repair and Regeneration, Miami, Jul.-Sep. 1993, pp. 181-186.
Chardack W.M., et al., "Experimental Studies on Synthetic Substitutes for Skin and Their Use in the Treatment of Burns," Annals of Surgery, vol. 155(1), Mar. 1961, pp. 127-139.
Chariker M.E., et al., "Effective Management of Incisional and Cutaneous Fistulae with Closed Suction Wound Drainage," Contemporary Surgery, vol. 34, Jun. 1989, pp. 59-63.
Davydov Y A., et al., "Concepts for Clinical Biological Management of the Wound Process in the Treatment of Purulent Wounds Using Vacuum Therapy," Vestnik Khirugii, Feb. 1991, pp. 15-17.
Davydov Y. et al., "Vacuum Therapy in the Treatment of Purulent Lactation Mastitis," Russian Journal: Vesnik Khirurgii, Sep. 1986, pp. 66-70.
Davydov Y.A., et al., "The Bacteriological and Cytological Assessment of Vacuum Therapy of Purulent Wounds," Vestnik Khirurgii, Oct. 1988, pp. 11-14.
Davydov Y.A., et al., "Vacuum Therapy in treatment of Acute Purulent Diseases of Soft Tissues and Purulent Wounds," Vestnik Khirurgii (Surgeon's Herald), MEDICINE Publishers, 1986, 5 pages.
Dilmaghani A., et al., "A Method for Closed Irrigation and Suction Therapy in Deep Wound Infections," Journal of Bone and Joint Surgery, Mar. 1969, vol. 51-A(2), pp. 323-342.
Edlich R.F., et al., "Evaluation of a New, Improved Surgical Drainage System", The American Journal of Surgery, vol. 149(2), Feb. 1985, pp. 295-298.
Fleischmann W., et al., "Vacuum Sealing: Indication, Technique, and Results," Eur J Orthop Surg Traumatol, vol. 5, 1995, pp. 37-40.
Fleischmann W., "Vacuum Sealing for Treatment of Problematical Wounds," University Surgical Clinic and Polyclinic—Accident Surgery Department, WundForum Spezial-IHW, 1994, 4 pages.
Fleischmann W., "Vakuumversiegelung zur Behandlung von Problemwunden" Wund Forum Spezial, (with English translation:

(56) References Cited

OTHER PUBLICATIONS

Vacuum Sealing for Treatment of Problematical Wounds), IHW '94, pp. 54-55 (6 pages with English translation).
Fujimori R., et al., "Sponge Fixation Method for Treatment of Early Scars," from the Department of Dermatology in the Faculty Medicine, Kyoto University, Plastic & Reconstructive Surgery, vol. 42, No. 4, Oct. 1968, pp. 322-326.
Garcia-Rinaldi R., et al., "Improving the Efficiency of Wound Drainage Catheters," American Journal of Surgery, Sep. 1975, vol. 130, pp. 372-373.
Greer S.E., et al., "Techniques for Applying Subatmospheric Pressure Dressing to Wounds in Difficult Regions of Anatomy," JWOCN, vol. 26(5), Sep. 1999, pp. 250-253.
Grounds for the Decision, the Opposition of European Patent No. 2437802, dated Nov. 2, 2018, 42 pages.
Gunter et al., "Microbicidal Activity of a New Silver-Containing Polymer," SPI-ARGENT II, Antimicrobial Agents and Chemotherapy, Sep. 1998, pp. 2440-2442.
Health Technology Literature Review, "Vacuum Assisted Closure Therapy for Wound Care," The Medical Advisory Secretariat, Dec. 2004, pp. 1-57.
Hough M.C. et al., "The Plastics Compendium—Comparative Materials Selection Data," vol. 2, Rapra Technology Ltd., 1998, 4 pages.
International Search Report and Written Opinion for PCT Application No. PCT/US2009/46889, dated Jul. 17, 2009, 8 pages.
International Preliminary Report on Patentability for Application No. PCT/US2009/046580, dated Dec. 15, 2011, 6 pages.
International Preliminary Report on Patentability for Application No. PCT/US2010/061938, dated Jun. 26, 2012, 11 pages.
International Preliminary Report on Patentability for PCT Application No. PCT/US2009/46889, dated Feb. 3, 2011, 7 pages.
International Search Report and Written Opinion for Application No. PCT/US2009/046580, dated Jul. 29, 2009, 6 pages.
International Search Report and Written Opinion for Application No. PCT/US2010/061938, dated Sep. 8, 2011, 10 pages.
International Search Report and Written Opinion for Application No. PCT/US2011/041521, dated Oct. 7, 2011, 15 pages.
Jeter K F., et al., "Managing Draining Wounds and Fistulae: New and Established Methods," Chronic Wound Care, Chapter 27, 1990, pp. 240-246.
KCI Inc., "Basic Application Guide for VAC Dressings for Wounds Without Exposed Vessels, Organs, Tendons and Nerves," 2008, 2 pages.
KCI Inc., "VAC Abdominal Dressing System: An Advanced Dressing for Managing the Open Abdomen," 2006, 6 pages.
KCI Inc., "V.A.C.® Therapy Clinical Guidelines, A Reference Source for Clinicians," KCI The Clinical Advantage, Jul. 2007, 92 pages.
KCI, "V.A.C. Therapy Clinical guidelines: A reference source for clinicians," Nov. 2005, 24 pages.
KCI, "V.A.C. therapy, GranuFoam Bridge Dressing Product," Brochure, 2009, 2 pages.
Kendall ULTEC Hydrocolloid Dressing (4x4"), Product Ordering Page, web page downloaded on Jul. 13, 2014, 1 page.
Kostiuchenok B.M., et al., "The Vacuum Effect in the Surgical Treatment of Purulent Wounds," Russian Journal: Vestnik Khirurgii, Sep. 1986, pp. 18-21.
McLaughlan J., et al., "Sterile Microenvironment for Postoperative Wound Care," The Lancet, Sep. 2, 1978, pp. 503-504.
Meyer W., et al., "In Surgery, Medicine and the Specialties a Manual of its Practical Application", Bier's Hyperemic Treatment, Second Revised Edition, W.B. Saunders Company, 1909, 72 pages.
Morykwas M.J., et al., "Vacuum-Assisted Closure: A New Method for Wound Control and Treatment: Animal Studies and Basic Foundation," Annals Plastic Surgery, vol. 38 (6), Jun. 1997, pp. 553-562.
Mulder G.D., et al., "Clinicians' Pocket Guide to Chronic Wound Repair," Wound Healing Publications, Second Edition, 1991, pp. 54-55 (4 pages).

Notice of Opposition—Statement of Facts and Evidence of the European Patent No. 2437802, dated Jan. 23, 2017, 164 pages.
Pentair Pool Products, "2000 Series Stainless Steel D. E. Filters," 2006, 2 pages.
Protz K., "Modern Wound Dressings Support the Healing Process," Wound care: Indications and Application, Geriatrie Journal, Apr. 2005,pp. 3333-3339 (17 pages with English translation).
Renasys E. Z., "System for Negative Wound Therapy, Smith & Nephew announcement," dated Feb. 24, 2009, 3 pages.
Sames C.P., "Sealing of Wounds with Vacuum Drainage", British Medical Journal, Nov. 5, 1977, p. 1223.
Sanden G.M.D. et al., "Staphylococcal Wound Infection in the Pig: Part II. Inoculation, Quantification of Bacteria, and Reproducibility," Annals of Plastic Surgery, vol. 23(3), Sep. 1989, pp. 219-223.
Smith S.R.G., "Surgical Drainage," Surgical symposium, British Journal of Hospital Medicine, Jun. 1985, pp. 308-315.
Stewart J., "World Wide Wounds—Next Generation of Products for Wound Management," Nov. 2002, http://www.worldwidewounds.com/2003/aprii/Stewart/Next-Generation-Products.html, 13 pages.
Stoll S., "Energetic Remedies—Cupping: Healing Within A Vacuum," https://www.suite101.com/article.cfm/energetic_remedies/74531, Apr. 13, 2005, 4 pages.
Svedman P., "A Dressing Allowing Continuous Treatment of a Biosurface," IRCS Medical Science: Biomedical Technology; Clinical Medicine; Surgery and Transplantation, vol. 7, 1979, p. 221.
Svedman P., et al., "A Dressing System Providing Fluid Supply and Suction Drainage Used for Continuous or Intermittent Irrigation," Annals of Plastic Surgery, vol. 17 (2), Aug. 1986, 9 pages.
Svedman P., et al., "Staphylococcal Wound Infection in the Pig: Part I. Course," Annals of Plastic Surgery, vol. 23 (3), Sep. 1989, pp. 212-218.
Svedman P., "Irrigation Treatment of Leg Ulcers," The Lancet, Sep. 3, 1983, pp. 532-534.
Teder H., et al., "Continuous Wound Irrigation in the Pig," Journal of Investigative Surgery, 1990, vol. 3, pp. 399-407.
Tribble D E., "An Improved Sump Drain-Irrigation Device of Simple Construction," Archives of Surgery, vol. 105, Sep. 1972, pp. 511-513.
Usupov Y. N., et al., "Active Wound Drainage," Russian Journal: Vestnik Khirurgii, Apr. 1987 (p. 42-45), Perspectives in Wound Care, BlueSky Publishing, pp. 8-10.
Van Way, C.W., "Prevention of Suction-Induced Gastric Mucosal Damage in Dogs," Crital Care Medicine, vol. 15, No. 8, Aug. 1987, pp. 774-777.
Wooding-Scott M., et al., "No Wound is Too Big for Resourceful Nurses," RN, Dec. 1988, pp. 22-25.
Worth M.H., et al., "The Effectiveness of Bacterial Filtration in Vented Wound Drains," Journal of Surgical Research, vol. 27(6), Dec. 1979, pp. 405-407.
Written Submission in Response to the Summons to Oral Proceedings, Opposition of European Patent No. 2437802, dated May 25, 2018, 38 pages.
Written Submissions in Preparation to Oral Proceedings, re the Opposition of European Patent No. 2437802, dated Apr. 17, 2018, 30 pages.
Wu S.H., et al., "Vacuum Therapy as an Intermediate Phase in Wound Closure: A Clinical Experience," Eur J Plast Surg, 2000, vol. 23, pp. 174-177.
Zivadinovic G., et al., "Vacuum Therapy in the Treatment of Peripheral Blood Vessels," Timocki Medicinski Glasnik, Conference Papers of the 5th Timok Medical Days, Majdanpek, No. 3-4, 1986, pp. 161-164.
KCI, Inc., "NPWT | Basic V.A.C. Therapy Application | KCI", link to YouTube video re same, uploaded to YouTube on Sep. 23, 2011, found at: http://www.youtube.com/watch?v=ucHAM_ZEIzs, 1 page.
U.S. Appl. No. 12/044,051, Wound Dressing Port and Associated Wound Dressing, filed Mar. 7, 2008.
U.S. Appl. No. 14/688,275, Wound Dressing Port and Associated Wound Dressing, filed Apr. 16, 2015.
U.S. Appl. No. 15/967,417, Wound Dressing Port and Associated Wound Dressing, filed Apr. 30, 2018.
U.S. Appl. No. 16/120,056, System for Providing Wound Dressing Port and Associated Wound Dressing, filed Aug. 31, 2018.

(56) References Cited

OTHER PUBLICATIONS

U.S. Appl. No. 17/900,671, System for Providing Wound Dressing Port and Associated Wound Dressing, filed Aug. 31, 2022.
U.S. Appl. No. 12/176,773, Thin Film Wound Dressing, filed Jul. 21, 2008.
U.S. Appl. No. 13/218,689, Thin Film Wound Dressing, filed Aug. 26, 2011.
U.S. Appl. No. 14/696,211, Thin Film Wound Dressing, filed Apr. 24, 2015.
U.S. Appl. No. 16/029,369, Thin Film Wound Dressing, filed Jul. 6, 2018.
U.S. Appl. No. 12/475,954, System for Providing Continual Drainage in Negative Pressure Wound Therapy, filed Jun. 1, 2009.
U.S. Appl. No. 13/571,548, System for Providing Continual Drainage in Negative Pressure Wound Therapy, filed Aug. 10, 2012.
U.S. Appl. No. 14/333,026, System for Providing Continual Drainage in Negative Pressure Wound Therapy, filed Jul. 16, 2014.
U.S. Appl. No. 15/872,810, System for Providing Continual Drainage in Negative Pressure Wound Therapy, filed Jan. 16, 2018.
U.S. Appl. No. 17/087,088, System for Providing Continual Drainage in Negative Pressure Wound Therapy, filed Nov. 2, 2020.
U.S. Appl. No. 15/865,641, Wound Treatment Apparatus and Method, filed Jan. 9, 2018.
U.S. Appl. No. 14/267,636, Apparatuses and Methods for Negative Pressure Wound Therapy, filed May 1, 2014.
U.S. Appl. No. 15/018,724, Apparatuses and Methods for Negative Pressure Wound Therapy, filed Feb. 8, 2016.
U.S. Appl. No. 15/198,690, Apparatuses and Methods for Negative Pressure Wound Therapy, filed Jun. 30, 2016.
U.S. Appl. No. 15/256,349, Apparatuses and Methods for Negative Pressure Wound Therapy, filed Sep. 2, 2016.
U.S. Appl. No. 15/681,165, Apparatuses and Methods for Negative Pressure Wound Therapy, filed Aug. 18, 2017.
U.S. Appl. No. 16/547,273, Apparatuses and Methods for Negative Pressure Wound Therapy, filed Aug. 21, 2019.
U.S. Appl. No. 16/590,278, Apparatuses and Methods for Negative Pressure Wound Therapy, filed Oct. 1, 2019.
U.S. Appl. No. 17/752,745, Apparatuses and Methods for Negative Pressure Wound Therapy, filed May 24, 2022.
U.S. Appl. No. 17/961,075, Apparatuses and Methods for Negative Pressure Wound Therapy, filed Oct. 6, 2022.
U.S. Appl. No. 29/501,203, Suction Adapter, filed Sep. 2, 2014.
U.S. Appl. No. 29/547,295, Suction Adapter, filed Dec. 2, 2015.
U.S. Appl. No. 29/405,978, Suction Adapter, filed Nov. 8, 2011.
U.S. Appl. No. 13/381,885, Apparatuses and Methods for Negative Pressure Wound Therapy, filed Dec. 30, 2011.
U.S. Appl. No. 15/970,774, Apparatuses and Methods for Negative Pressure Wound Therapy, filed May 3, 2018.
U.S. Appl. No. 17/259,891, Apparatuses and Methods for Negative Pressure Wound Therapy, filed Jan. 12, 2021.
U.S. Appl. No. 18/372,577, Apparatuses and Methods for Negative Pressure Wound Therapy, filed Sep. 25, 2023.
U.S. Appl. No. 17/793,219, Fluidic Connectors for Negative Pressure Wound Therapy, filed Jul. 15, 2022.
Amazon, "Nexcare Waterproof Transparent Breathable Post Surgical," 2003, Retrieved from the Internet: URL: www.amazon.com/Nexcare-Waterproof-Transparent-Breathable-Post-Surgical/dp/B000GG7UEW.
Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.
Kinetic Concepts, Inc., "510K filing K022011 by KCI with the Food and Drug Administration," Jun. 19, 2002, 5 pages.
News., "KCI Launches Next Generation Wound Care Therapy Systems," Imaging Technology News, Aug. 30, 2007, Retrieved from Internet URL: https://www.itnonline.com/content/kci-launches-next-generation-wound-car-etherapy-systems, 2 pages.
Technology Watch, May 1989, 1 page.
The Wayback Machine, "Comfort advantages with AirX™," retrieved from http://web.archive.org/web/20090121000205/http://www.airx.eu:80/content/view/2/3/lang,en/, on Jan. 21, 2009, 1 page.
The Wayback Machine, "Comfort advantages with AirX™," Retrieved from the Internet: https://web.archive.org/web/20070714011844/http://www.air-x.net/content/view/2/3/lang/, on Jul. 14, 2007, 1 page.
The Wayback Machine, "Moisture-Transporting Material," retrieved from http://web.archive.org/web/20090121001036/http://www.airx.eu/content/view/1/14/lang,en/, on Jan. 21, 2009, 1 page.
The Wayback Machine, "Moisture-Transporting Material," Retrieved from the Internet: https://web.archive.org/web/20070714011837/http://www.air-x.net/content/view/1/2/lang/, on Jul. 14, 2007, 1 page.
Images of SensaT.R.A.C. produced in 2016, filed in Post Grant Review of U.S. Pat. No. 9,642,750 dated Feb. 9, 2018, in 5 pages.
Trademark Prosecution History for SENSAT.R.A.C. filed in Post Grant Review of U.S. Pat. No. 9,642,750 dated Feb. 9, 2018, in 112 pages.
Advantec MFS, Inc., "Membrane Filters" (catalog), retrieved from http://www.advantecmfs.com/catalog/filt/membrane.pdf, on Jan. 29, 2016, Copyright 2001-2011, 17 pages.
Wikipedia, "Gauze," Retrieved from https://en.wikipedia.org/wiki/index.php?title=Gauze&oldid=1144188198, latest edit Mar. 12, 2023, 3 pages.
Wikipedia, "Parallel (geometry)," retrieved from https://en.wikipedia.org/w/index.php?title=Parallel_(geometry)&oldid=1080576469, last edited on Apr. 2, 2022, 9 pages.

* cited by examiner

SYSTEM FOR PROVIDING CONTINUAL DRAINAGE IN NEGATIVE PRESSURE WOUND THERAPY

BACKGROUND

1. Technical Field

The present disclosure relates generally to treating a wound with negative or reduced pressure. In particular, the disclosure relates to a system for providing continual drainage of fluids from a wound site to a collection canister.

2. Background of Related Art

Various techniques to promote healing of a wound involve providing suction to the wound. For example, a vacuum source may serve to carry wound exudates away from the wound, which may otherwise harbor bacteria that inhibit the body's natural healing process. One particular technique for promoting the body's natural healing process may be described as negative pressure wound therapy (NPWT). This technique involves the application of a reduced pressure, e.g. sub-atmospheric, to a localized reservoir over a wound. Sub-atmospheric pressure has been found to assist in closing the wound by promoting blood flow to the area, thereby stimulating the formation of granulation tissue and the migration of healthy tissue over the wound. This technique has proven effective for chronic or non-healing wounds, but has also been used for other purposes such as post-operative wound care.

The general NPWT protocol provides for covering the wound with a flexible cover layer such as a polymeric film, for example, to establish a vacuum reservoir over the wound where a reduced pressure may be applied by individual or cyclic evacuation procedures. To allow the reduced pressure to be maintained over time, the cover layer may include an adhesive periphery that forms a substantially fluid tight seal with the healthy skin surrounding the wound.

Although some procedures may employ a micro-pump contained within the vacuum reservoir, most NPWT treatments apply a reduced pressure using an external vacuum source. Fluid communication must therefore be established between the reservoir and the vacuum source. To this end, a fluid port is coupled to the cover layer to provide an interface for an exudate conduit extending from the external vacuum source. Fluid being drained from the reservoir through the exudate conduit tends to stagnate with slow fluid buildup. This stagnation results in interrupted and/or incomplete fluid drainage. Accordingly, it would be beneficial to have a negative pressure wound therapy system that included a controlled or fixed "leak" to provide for continuous and/or complete fluid drainage.

SUMMARY

A system for subatmospheric pressure therapy in connection with healing a wound is provided. The system includes a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a vent conduit in fluid communication with the collection canister and the wound dressing for introducing air into the reservoir to facilitate flow of exudate through the exudate conduit.

The vent conduit may define an internal dimension less than a corresponding internal dimension of the exudate conduit. The exudate conduit and the vent conduit may include independent tube segments, or instead may include integral tube segments. A filter may be in fluid communication with the vent conduit. The filter includes a hydrophobic material. The filter may instead or additionally include a bacterial filter.

Also provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a vent mounted to the wound dressing, the vent being selectively movable between a closed position and an open position, the vent permitting ingress of air within the reservoir when in the open position.

The vent may include a flap mounted to the wound dressing cover, the flap being movable between the closed position and the open position. The flap may be releasably securable in the closed position with an adhesive. A filter membrane may be mounted adjacent the flap. The filter membrane may include a hydrophobic material. The filter membrane may instead or additionally include a bacterial filter.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system further includes an exudate conduit in fluid communication with the wound dressing and the collection canister for collecting exudate removed from the reservoir and deposited in the collection canister under influence of the vacuum source and a filtered air vent mounted to the wound dressing cover, the filtered air vent adapted to permit ingress of air within the reservoir to facilitate flow of exudate through the exudate conduit.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The wound port includes a vacuum port and at least one tube piercing through the wound port into the reservoir, the tube being operable to allow ambient air into the reservoir. The system further includes an exudate conduit in fluid communication with the wound port and the collection canister for collecting exudate removed from the reservoir and deposited in the collection canister under influence of the vacuum.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The wound port includes a vacuum port and a plurality of holes arranged circumferentially around the wound port, the plurality of holes being operable to allow ambient air into the reservoir. The system further includes an exudate conduit in fluid communication with the wound port and the collection canister for collecting exudate removed from the reservoir and deposited in the collection canister under influence of the vacuum.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The wound port includes a vacuum port and an orifice being operable to allow ambient air into the reservoir. The system further includes an exudate conduit in fluid communication with the wound port and the collection canister for collecting exudate removed from the reservoir and deposited in the collection canister under influence of the vacuum.

Additionally, provided is a system for subatmospheric pressure therapy in connection with healing a wound including a wound dressing cover dimensioned for positioning relative to a wound bed of a subject to establish a reservoir over the wound bed in which subatmospheric pressure may be maintained, a subatmospheric pressure mechanism including, a housing, a vacuum source disposed in the housing, and a collection canister in fluid communication with the vacuum source. The system also includes a wound port operatively connected to the wound dressing in fluid communication with the reservoir. The system further includes an exudate conduit in fluid communication with the wound port and the collection canister for collecting exudate removed from the reservoir and deposited in the collection canister under influence of the vacuum. The exudate conduit has a first conduit for providing a pathway for the exudate between the reservoir and the collection canister and a second conduit in fluid communication with ambient atmosphere and the wound dressing for introducing air into the reservoir to facilitate flow of exudate through the exudate conduit.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF EMBODIMENTS

Figure 1:
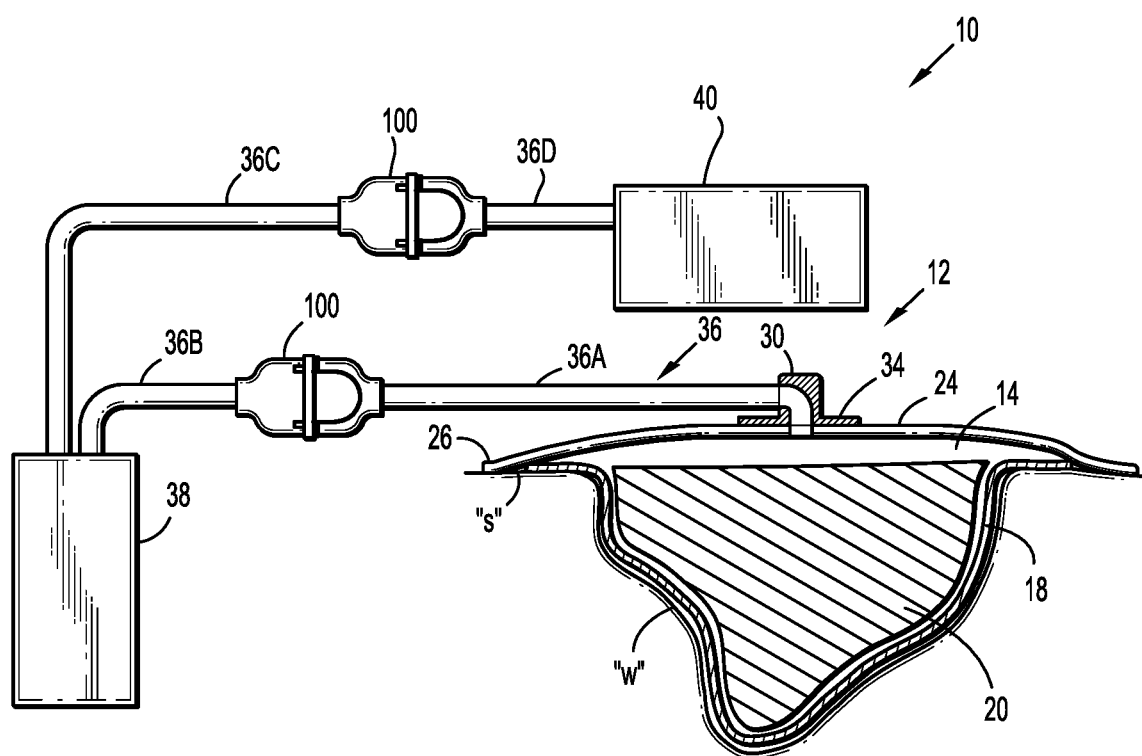
FIG. 1 depicts an embodiment of a NPWT system in accordance with the present disclosure.

Various embodiments of the present disclosure provide negative pressure wound therapy systems (or apparatus) including a collection canister having a chamber to collect wound fluids. Embodiments of the presently disclosed negative pressure wound therapy systems are generally suitable for use in applying negative pressure to a wound to facilitate healing of the wound in accordance with various treatment modalities. Embodiments of the presently disclosed negative pressure wound therapy systems are entirely portable and may be worn or carried by the user such that the user may be completely ambulatory during the therapy period. Embodiments of the presently disclosed negative pressure wound therapy apparatus and components thereof may be entirely reusable or may be entirely disposable after a predetermined period of use or may be individually disposable whereby some of the components are reused for a subsequent therapy application.

Hereinafter, embodiments of the presently disclosed negative pressure wound therapy systems and embodiments of the presently disclosed sensors for use in negative pressure wound therapy systems will be described with reference to the accompanying drawings. Like reference numerals may refer to similar or identical elements throughout the description of the figures. As used herein, "wound exudate", or, simply, "exudate", generally refers to any fluid output from a wound, e.g., blood, serum, and/or pus, etc. As used herein, "fluid" generally refers to a liquid, a gas or both.

Referring to FIG. 1, a NPWT apparatus according to an embodiment of the present disclosure is depicted generally as 10 for use on a wound bed "w" surrounded by healthy skin "s". Negative pressure wound therapy apparatus 10 includes a wound dressing 12 positioned relative to the wound bed "w" to define a vacuum chamber 14 about the wound bed "w" to maintain negative pressure at the wound area. Wound dressing 12 includes a contact layer 18, a wound filler 20 and a wound cover 24.

Contact layer 18 is intended for placement within the wound bed "w" and may be relatively non-supportive or flexible to substantially conform to the topography of the wound bed "w". A variety of materials may be used for the contact layer 18. Contact layer 18 selection may depend on various factors such as the patient's condition, the condition of the periwound skin, the amount of exudate and/or the condition of the wound bed "w". Contact layer 18 may be formed from perforated film material. The porous characteristic of the contact layer 18 permits exudate to pass from the wound bed "w" through the contact layer 18. Passage of wound exudate through the contact layer 18 may be substantially unidirectional such that exudate does not tend to flow back into the wound bed "w". Unidirectional flow may be encouraged by directional apertures, e.g., apertures positioned at peaks of undulations or cone-shaped formations protruding from the contact layer 18. Unidirectional flow may also be encouraged by laminating the contact layer 18 with materials having absorption properties differing from those of the contact layer 18, or by selection of materials that promote directional flow. A non-adherent material may be selected for forming the contact layer 18 such that the contact layer 18 does not tend to cling to the wound bed "w" or surrounding tissue when it is removed. One example of a material that may be suitable for use as a contact layer 18 is commercially available under the trademark XEROFLOW® offered by Tyco Healthcare Group LP (d/b/a Covidien). Another example of a material that may be suitable for use as the contact layer 18 is the commercially available CURITY® non-adherent dressing offered by Tyco Healthcare Group LP (d/b/a Covidien).

Wound filler 20 is positioned in the wound bed "w" over the contact layer 18 and is intended to transfer wound exudate. Wound filler 20 is conformable to assume the shape of any wound bed "w" and may be packed up to any level, e.g., up to the level of healthy skin "s" or to overfill the wound such that wound filler 20 protrudes over healthy skin "s". Wound filler 20 may be treated with agents such as polyhexamethylene biguanide (PHMB) to decrease the incidence of infection and/or other medicaments to promote wound healing. A variety of materials may be used for the wound filler 20. An example of a material that may be suitable for use as the wound filler 20 is the antimicrobial dressing commercially available under the trademark KERLIX™ AMD™ offered by Tyco Healthcare Group LP (d/b/a Covidien).

Cover layer 24 may be formed of a flexible membrane, e.g., a polymeric or elastomeric film, which may include a biocompatible adhesive on at least a portion of the cover layer 24, e.g., at the periphery 26 of the cover layer 24. Alternately, the cover layer 24 may be a substantially rigid member. Cover layer 24 may be positioned over the wound bed "w" such that a substantially continuous band of a biocompatible adhesive at the periphery 26 of the cover layer 24 forms a substantially fluid-tight seal with the surrounding skin "s". An example of a material that may be suitable for use as the cover layer 24 is commercially available under the trademark CURAFORM ISLAND® offered by Tyco Healthcare Group LP (d/b/a Covidien).

Cover layer 24 may act as both a microbial barrier and a fluid barrier to prevent contaminants from entering the wound bed "w" and to help maintain the integrity thereof.

In one embodiment, the cover layer 24 is formed from a moisture vapor permeable membrane, e.g., to promote the exchange of oxygen and moisture between the wound bed "w" and the atmosphere. An example of a membrane that may provide a suitable moisture vapor transmission rate (MVTR) is a transparent membrane commercially available under the trade name POLYSKIN® II offered by Tyco Healthcare Group LP (d/b/a Covidien). A transparent membrane may help to permit a visual assessment of wound conditions to be made without requiring removal of the cover layer 24.

Wound dressing 12 may include a vacuum port 30 having a flange 34 to facilitate connection of the vacuum chamber 14 to a vacuum system. Vacuum port 30 may be configured as a rigid or flexible, low-profile component and may be adapted to receive a conduit 36 in a releasable and fluid-tight manner. An adhesive on at least a portion of the underside of the flange 34 may be used to provide a mechanism for affixing the vacuum port 30 to the cover layer 24. The relative positions, size and/or shape of the vacuum port 30 and the flange 34 may be varied from an embodiment depicted in FIG. 1. For example, the flange 34 may be positioned within the vacuum chamber 14 such that an adhesive on at least a portion of an upper side surface of the flange 34 affixes the vacuum port 30 to the cover layer 24. A hollow interior portion of the vacuum port 30 provides fluid communication between the conduit 36 and the vacuum chamber 14. Conduit 36 extends from the vacuum port 30 to provide fluid communication between the vacuum chamber 14 and the vacuum source 40. Alternately, the vacuum port 30 may not be included in the dressing 12 if other provisions are made for providing fluid communication with the conduit 36.

Any suitable conduit may be used for the conduit 36, including conduit fabricated from flexible elastomeric or polymeric materials. In the negative pressure wound therapy apparatus 10 illustrated in FIG. 1, the conduit 36 includes a first conduit section 36A, a second conduit section 36B, a third conduit section 36C and a fourth conduit section 36D. The first conduit section 36A extends from the vacuum port 30 and is coupled via a fluid line coupling 100 to the second conduit section 36B, which extends to the collection canister 38. The third conduit section 36C extends from the collection canister 38 and is coupled via another fluid line coupling 100 to the fourth conduit section 36D, which extends to the vacuum source 40. The shape, size and/or number of conduit sections of the conduit 36 may be varied from the first, second, third and fourth conduit sections 36A, 36B, 36C and 36D depicted in FIG. 1.

The first, second, third and fourth conduit sections 36A, 36B, 36C and 36D of the conduit 36 may be connected to components of the apparatus 10 by conventional air-tight means, such as, for example, friction fit, bayonet coupling, or barbed connectors. The connections may be made permanent. Alternately, a quick-disconnect or other releasable connection means may be used to provide some adjustment flexibility to the apparatus 10.

Collection canister 38 may be formed of any type of container that is suitable for containing wound fluids. For example, a semi-rigid plastic bottle may be used for the collection canister 38. A flexible polymeric pouch or other hollow container body may be used for the collection canister 38. Collection canister 38 may contain an absorbent material to consolidate or contain the wound fluids or debris. For example, super absorbent polymers (SAP), silica gel, sodium polyacrylate, potassium polyacrylamide or related compounds may be provided within collection canister 38. At least a portion of canister 38 may be transparent or semi-transparent, e.g., to permit a visual assessment of the wound exudate to assist in evaluating the color, quality and/or quantity of exudate. A transparent or semi-transparent portion of the collection canister 38 may permit a visual assessment to assist in determining the remaining capacity or open volume of the canister and/or may assist in determining whether to replace the collection canister 38.

The collection canister 38 is in fluid communication with the wound dressing 12 via the first and second conduit sections 36A, 36B. The third and fourth conduit sections 36C, 36D connect the collection canister 38 to the vacuum source 40 that generates or otherwise provides a negative pressure to the collection canister 38. Vacuum source 40 may include a peristaltic pump, a diaphragmatic pump or other suitable mechanism. Vacuum source 40 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg to about 125 mmHg, or about 40 mmHg to about 80 mmHg One example of a peristaltic pump that may be used as the vacuum source 40 is the commercially available Kangaroo PET Eternal Feeding Pump offered by Tyco Healthcare Group LP (d/b/a Covidien). Vacuum source 40 may be actuated by an actuator (not shown) which may be any means known by those skilled in the art, including, for example, alternating current (AC) motors, direct current (DC) motors, voice coil actuators, solenoids, and the like. The actuator may be incorporated within the vacuum source 40.

In embodiments, the negative pressure wound therapy apparatus 10 includes one or more fluid line couplings 100 that allow for selectable coupling and decoupling of conduit sections. For example, a fluid line coupling 100 may be used to maintain fluid communication between the first and second conduit sections 36A, 36B when engaged, and may interrupt fluid flow between the first and second conduit sections 36A, 36B when disengaged. Thus, fluid line coupling 100 may facilitate the connection, disconnection or maintenance of components of the negative pressure wound therapy apparatus 10, including the replacement of the collection canister 38. Additional or alternate placement of one or more fluid line couplings 100 at any location in line with the conduit 36 may facilitate other procedures. For example, the placement of a fluid line coupling 100 between the third and fourth conduit sections 36C, 36D, as depicted in FIG. 1, may facilitate servicing of the vacuum source 40.

Figure 2:
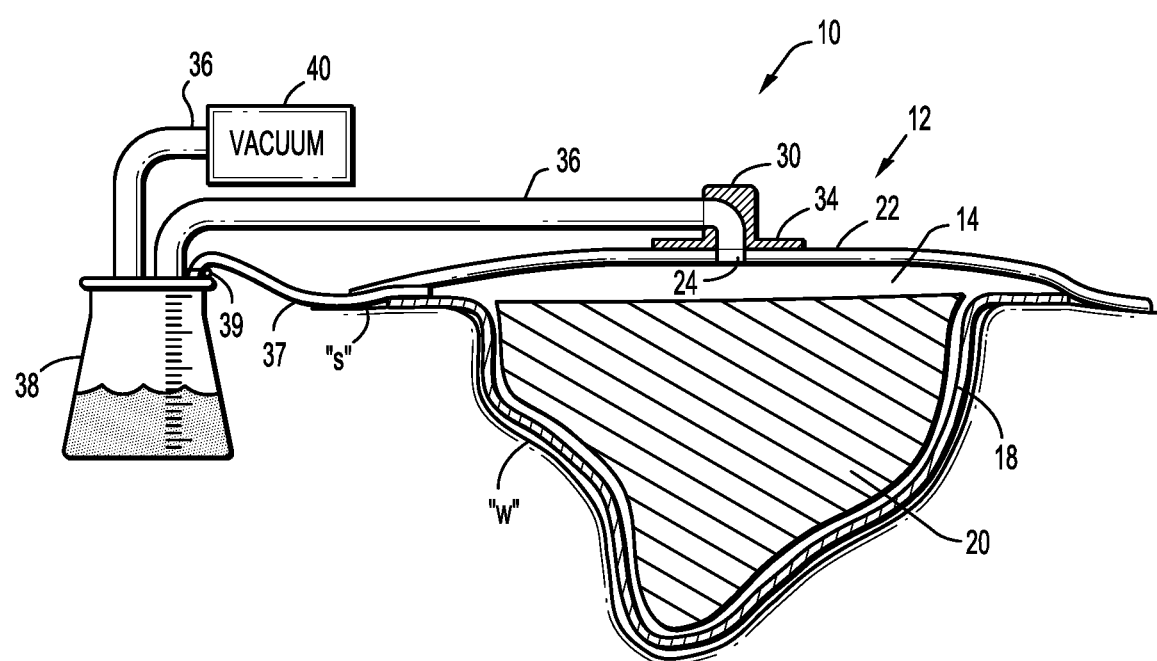
FIG. 2 depicts an embodiment of an NPWT treatment apparatus including a vent conduit.

Referring to FIG. 2, an NPWT apparatus similar to the NPWT apparatus of FIG. 1 is depicted generally as 10 for use on a wound "w" surrounded by healthy skin "s." The NPWT apparatus 10 of FIG. 2 includes a vent conduit 37 that extends from between contact layer 18 and cover layer 22 of wound dressing 12 to collection canister 38. Vent conduit 37 may be integral formed with wound dressing 12. Alternatively, vent conduit 37 may be inserted between contact layer 18 and cover layer 22 by a clinician during application of the wound dressing 12, or may have been previously inserted therebetween prior to application. Vent conduit 37 may be releasably connected to the collection canister 38 by conventional air-tight means such as friction fit, bayonet coupling, or barbed connectors.

Vent conduit 37 is configured to provide a low flow of air from the reservoir 14 to the collection canister 38. Vent conduit 37 includes a smaller diameter than exudate conduit 36 and may be formed of any suitable conduit including those fabricated from flexible elastomeric or polymeric materials. An air filter 39 positioned along the air flow path filters the air flowing from collection canister 38 to remove any impurities, including bacteria and other infectious material. Filter 39 may include a hydrophobic material to prevent wetting.

In operation, wound dressing 12 is placed adjacent a wound "w" with the vent conduit 37 extending from between the contact layer 18 and the cover layer 22. If the vent conduit 37 is not integral formed with the wound dressing 12, the clinician may be required to position the vent conduit 37 between the layers during application of the wound dressing 12. Vacuum source 50 is then activated to produce a sub-atmospheric pressure in the reservoir 14 of the wound dressing 12. Fluid from the reservoir 14 is drawn through aperture 24 in cover layer 22, into fluid port 30 and along exudate conduit 36 to be deposited in collection canister 40. As fluid and other exudates are drawn through exudate conduit 36, filtered air is received within the reservoir 14 of the wound dressing 12 through the vent conduit 37. The low flow filtered air flowing from the collection canister 38 through the vent conduit 37, in combination with the high flow drainage occurring through exudate conduit 36, creates a sump action between the reservoir 14 and the collection canister 40. This sump action ensures continuous flow through exudate conduit 36, thereby preventing fluid stagnation and its complications. Because of capillary action, fluid from reservoir 14 only flows through the larger diameter exudate conduit 36.

Figure 3A:
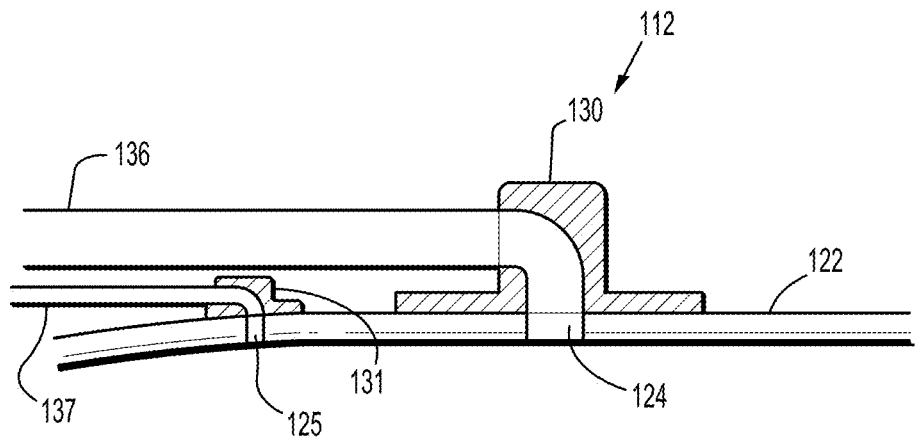
FIG. 3A is a partial cross sectional view of the conduits of the NPWT treatment apparatus of FIGS. 1 and 2 connected in an alternate configuration.

With reference now to FIG. 3A, in an alternative embodiment of the present disclosure, a wound dressing 112 is substantially similar to wound dressing 12 described hereinabove, and will only be described as relates to the differences therebetween. Wound dressing 112 includes a cover layer 122 having a first or fluid aperture 124 and a second or vent aperture 125. A fluid port 130 is in fluid communication with fluid aperture 124 and is configured for operable engagement with exudate conduit 136. A vent port 131 is in fluid communication with vent aperture 125 and is configured for operable engagement with vent conduit 137. Fluid and vent ports 130, 131 may be affixed to cover layer 122 in any suitable manner. Each of fluid and vent ports 130, 131 are in fluid communication with collection canister 38 (FIGS. 1 and 2).

Wound dressing 112 operates in substantially the same manner as wound dressing 12. When connected to collection canister 40 and the vacuum source 50 is activated, the sub-atmospheric pressure produced by the vacuum source 50 creates a suction that draws fluid from the reservoir 114. Vent conduit 137 provides the reservoir 114 with a low flow of filtered air to ensure continuous fluid flow through the exudate conduit 136.

Figure 3B:
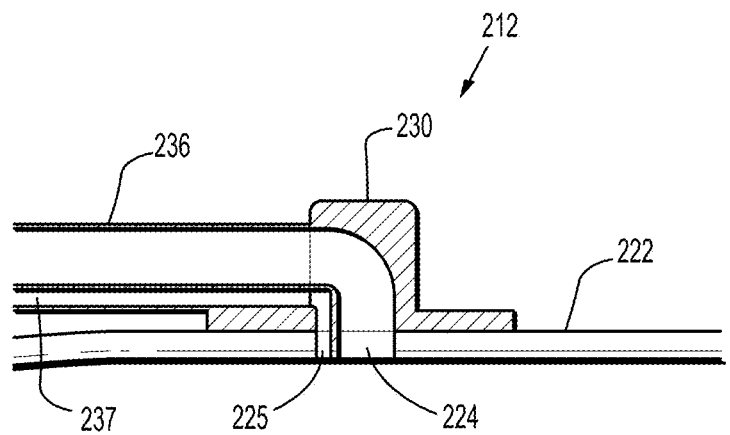
FIG. 3B is a partial cross sectional view of an alternative embodiment of the fluid port of FIGS. 1 and 2.

Turning now to FIG. 3B, in another embodiment, wound dressing 212 is substantially similar to the wound dressings 12, 112 described hereinabove. Wound dressing 212 includes a cover layer 222 having a first and second aperture 224, 225. Positioned adjacent first and second apertures 224, 225 is a fluid/vent port 230. Port 230 is configured to fluidly communicate first aperture 224 of wound dressing 212 with collection canister 38 (FIGS. 1 and 2) via exudate conduit 236. Port 230 is further configured to fluidly communicate second aperture 225 of wound dressing 212 with collection canister 40 via vent conduit 237. As discussed above, the difference in size between exudate conduit 236 and vent conduit 237 results in capillary action that causes fluid to flow only through the larger exudate conduit 36.

Figure 4:
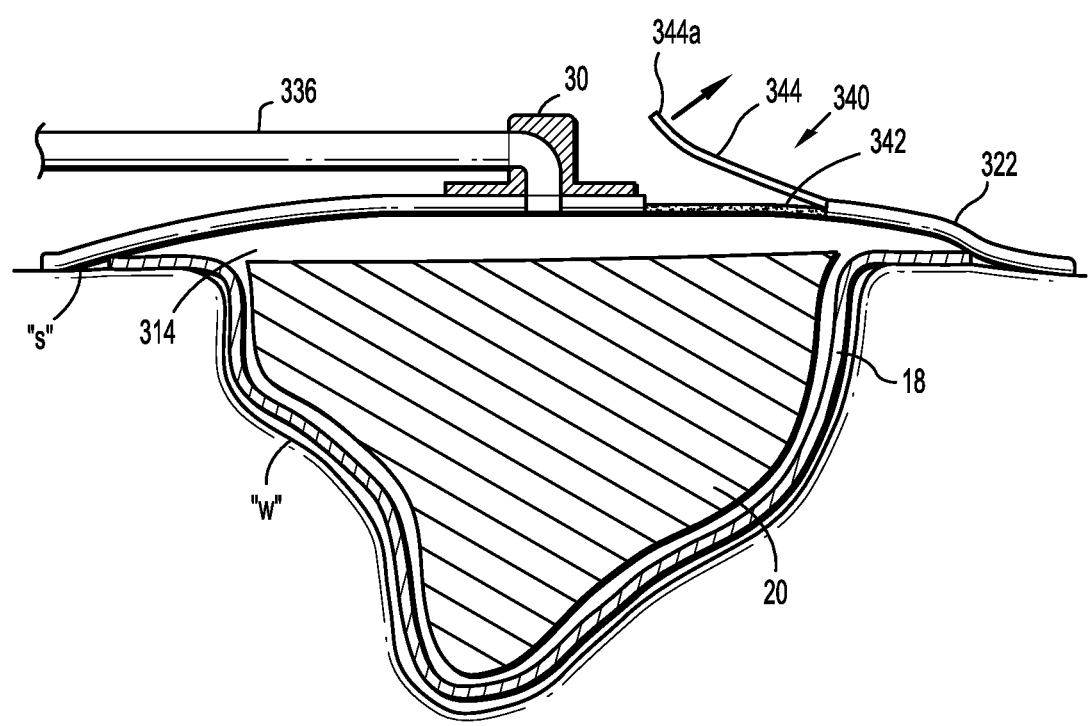
FIG. 4 is a cross sectional view of an alternative embodiment of the wound dressing in accordance with the present disclosure.

With reference now to FIG. 4, in yet another embodiment, a wound dressing 312 similar to those described above including a vent assembly 340 formed in a cover layer 322. Vent assembly 340 includes a filter member 342 and a flap or cover member 344. Filter member 342 may be integrally formed with, or otherwise affixed to, the cover layer 322. In one embodiment, filter member 342 is secured to the cover layer 322 with an adhesive. Filter member 342 is configured to provide reservoir 314 of wound dressing 312 with filtered air. To prevent wetting, the filter member 342 may be hydrophobic. Filter member 342 may be sized depending on the desired flow therethrough. A larger filter member 342 would provide a greater amount of airflow; however, if the filter member 342 is too large, it may reduce the effectiveness of the NWPT.

Flap 344 may be integrally formed with cover layer 322. Alternatively, flap 344 may be releasably secured over filter member 342. Flap 344 may be attached to or separable from cover member 322. Flap 344 may be configured to selectively partially or completely uncover filter member 342. In this manner, a clinician may affect the flow of air into the reservoir 314. Although shown including flap 344, it is envisioned that wound dressing 312 may be provided with filter member 342 exposed.

In use, wound dressing 312 is applied to a wound "w" in a conventional manner. Activation of the vacuum source 40 (FIGS. 1 and 2) initiates drainage from reservoir 314 of wound dressing 312. At any time prior to or during the drainage process, flap 344 may be partially or complete pulled back to expose filter member 342. As described above, the more of filter member 342 that is exposed, the greater the possible airflow into reservoir 14. The airflow provided to reservoir 14 through filter member 342 acts in a manner similar to the sump action described above. In this manner, vent assembly 340 permits continuous fluid flow through exudate conduit 336, thereby preventing fluid stagnation and its complications.

Figure 5A:
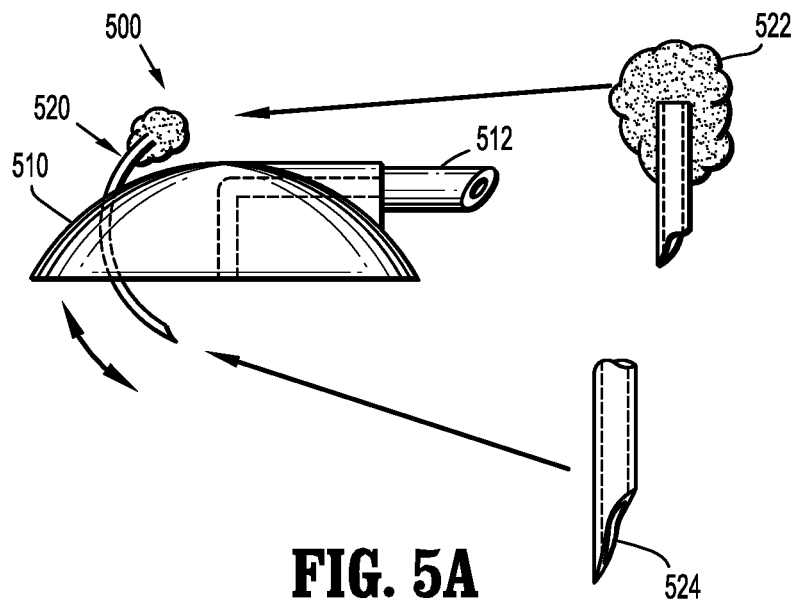
FIGS. 5A and 5B depict alternative embodiments of the wound dressing in accordance with the present disclosure.
Figure 5B:
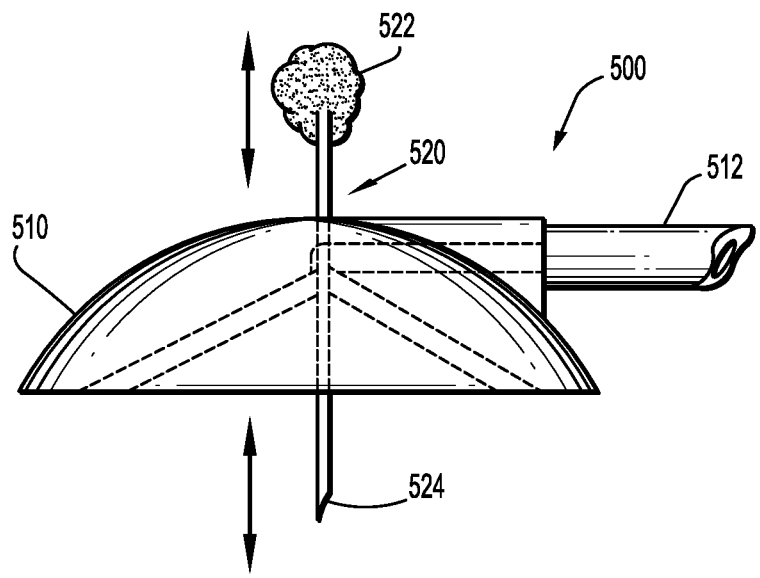

With reference to FIGS. 5A and 5B, in yet another embodiment, a wound port 500 is shown. Wound port 500 is suitable for use with the above described wound dressings. Wound port 500 has a plastic cover 510 which includes a vacuum port 512. In addition to the vacuum port 512, the plastic cover 510 has tube 520. Tube 520 may be made of a small-bore stainless steel or rigid plastic. Tube 520 is used to provide a controlled or fixed leak by admitting air into the wound dressing. Tube 520 can be arranged to allow the insertion of tube 520 into the wound port 500 so that depth adjustment and placement within the wound packing material is possible as indicated by the arrows in FIGS. 5A and 5B. As such, air can be injected into the wound packing material to direct movement of excess exudate toward the vacuum port and out of the wound. Tube 520 may have a valve (not shown) to adjust the flow rate of air into the wound bed. The valve may be a small needle valve that can be attached to the tube 520 to allow for infinite adjustment of air flow into the wound dressing.

The end of tube 520 that may be exposed to ambient atmosphere or to a source of air may include a filter 522. Filter 522 may be a q-tip like air filter to prevent clogging of the tube and also prevent dirt and other contaminants from entering the wound site. Alternatively, filter 522 may include a charcoal filter to prevent odor, a hydrophobic filter, or any sintered or porous material. The tip of tube 520 that is inserted into the wound packing material may be equipped with a puncturing tip 524 to allow for easier insertion into the wound packing material.

Figure 6A:
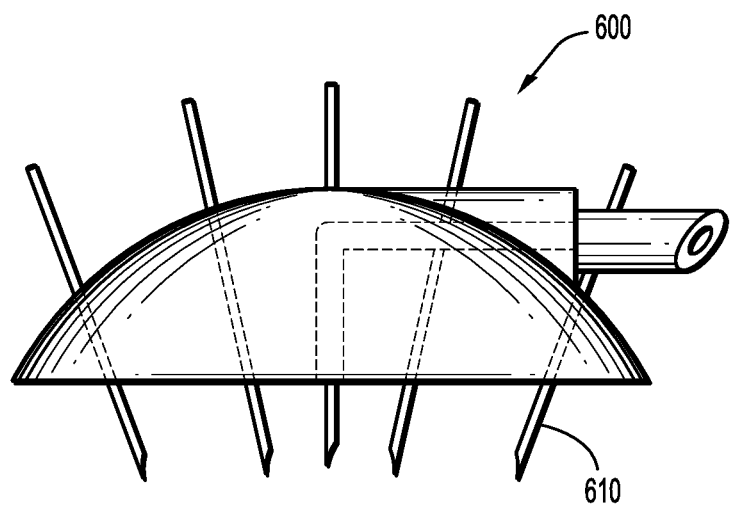
FIGS. 6A and 6B depict alternative embodiments of the wound dressing in accordance with the present disclosure.
Figure 6B:
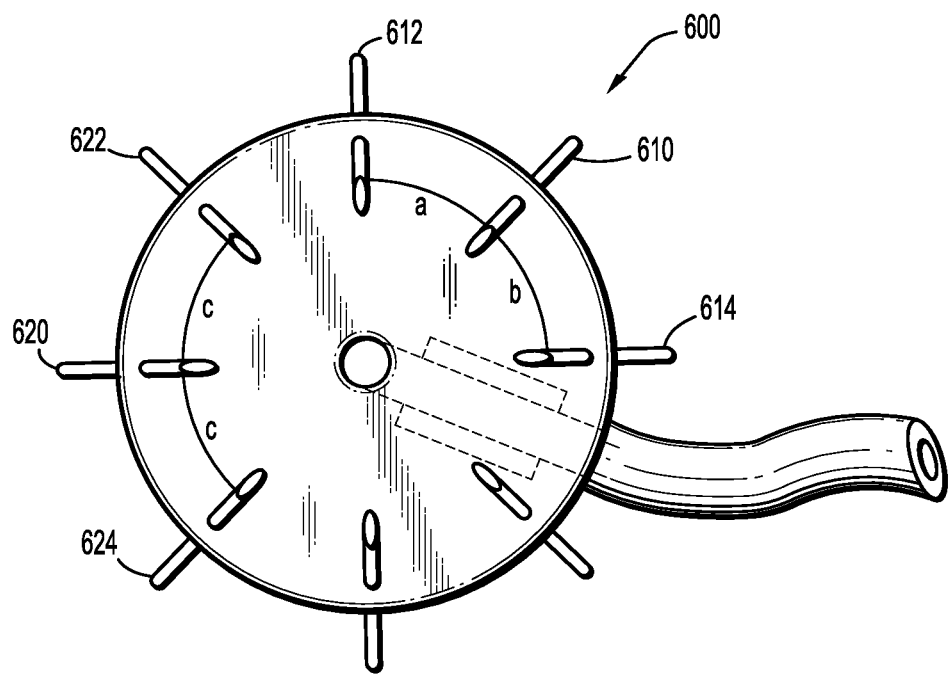

With reference to FIGS. 6A and 6B, in yet another embodiment, a wound port 600 is shown. As shown in FIG. 6A, wound port 600 has tube 610 in separate locations around a circumference of the wound port 600. Each tube may include a punctured tip or a filter as described above. As shown in FIG. 6B, the distance "a" between tube 610 and tube 612 may be one distance and the distance "b" between tube 610 and 614 may be a distance different the distance "a". On the other hand, the difference between each tube may be similar as in the distance "c" between tube 620 and 622 and tube 620 and 624. Although FIGS. 6A and 6B show a specific number of tubes, any number of tubes may be arranged outside a circumference of the wound port 600.

Figure 7A:
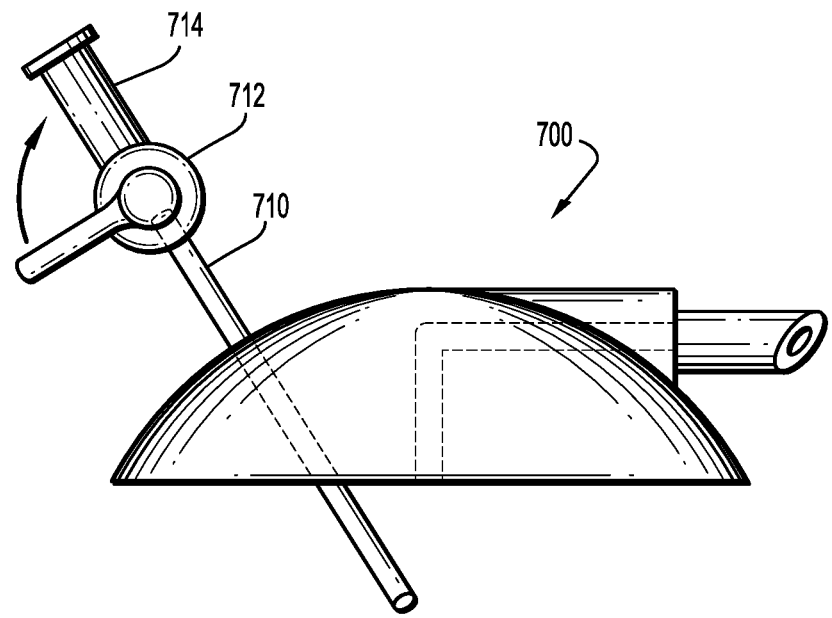
FIGS. 7A and 7B depict alternative embodiments of the wound dressing in accordance with the present disclosure.
Figure 7B:
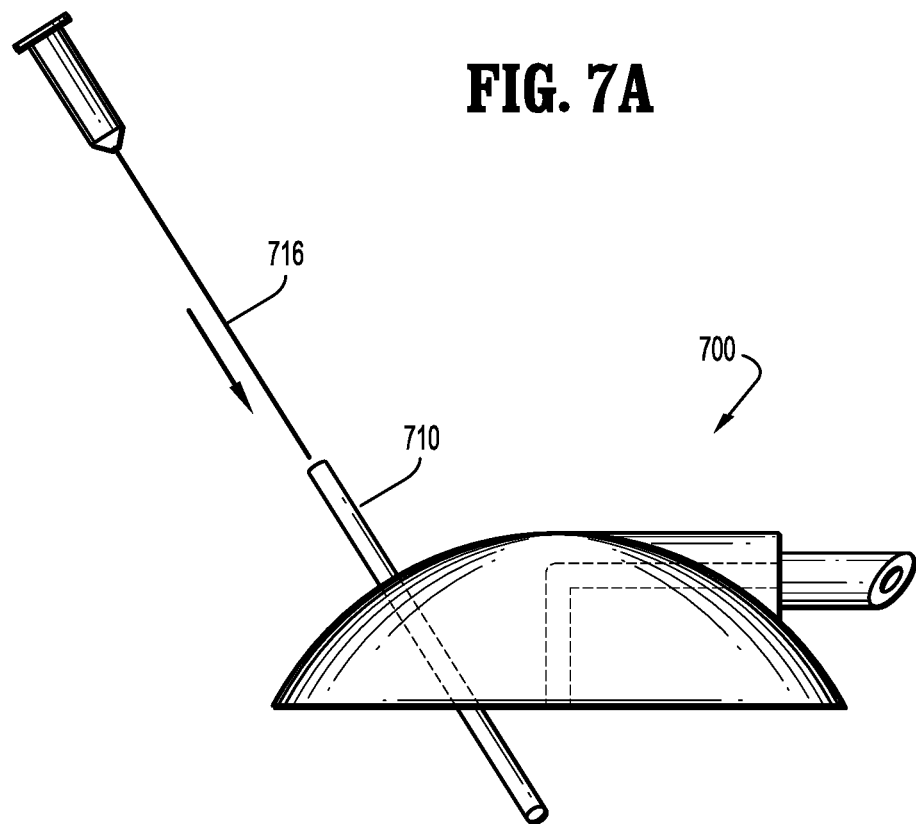

With reference to FIGS. 7A and 7B, in yet another embodiment, a wound port 700 is shown having a tube 710 which is similar to the tubes described above. Tube 710 may be slightly larger in diameter to allow for fluids to enter the wound site. The fluids may include a solution to flush the wound such as saline or it may be an anesthetic to anesthetize the wound area. Tube 710 may be fitted with valve 712 to open and close the pathway into the wound site. Additionally, the end of tube 710 may be fitted with a luer connector 714 to create a fluid tight connection with additional tubing, syringes, or any other conduits. Alternatively, instead of a valve, a plug (not shown) could be used to close the luer connector. With reference to FIG. 7B, a hypodermic needle 716 may be inserted into tube 710. Hypodermic needle 716 could be used to deliver a solution to a specific area of the wound or it could be used to obtain a sample of blood, exudate or tissue from the wound site.

Figure 8A:
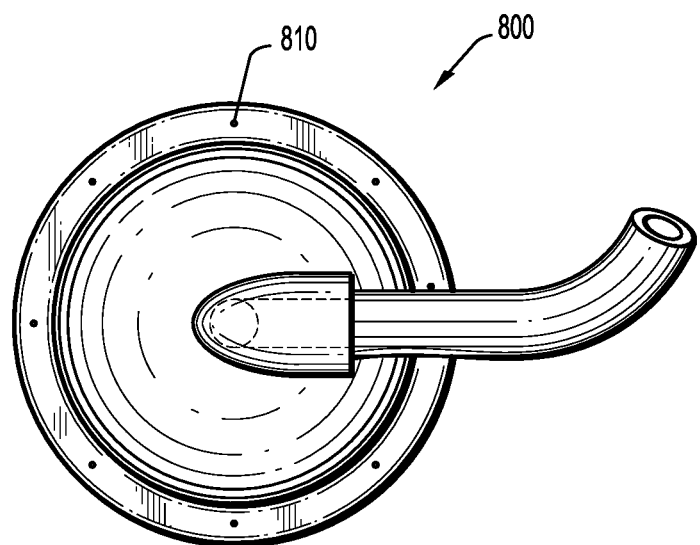
FIGS. 8A and 8B depict alternative embodiments of the wound dressing in accordance with the present disclosure.
Figure 8B:
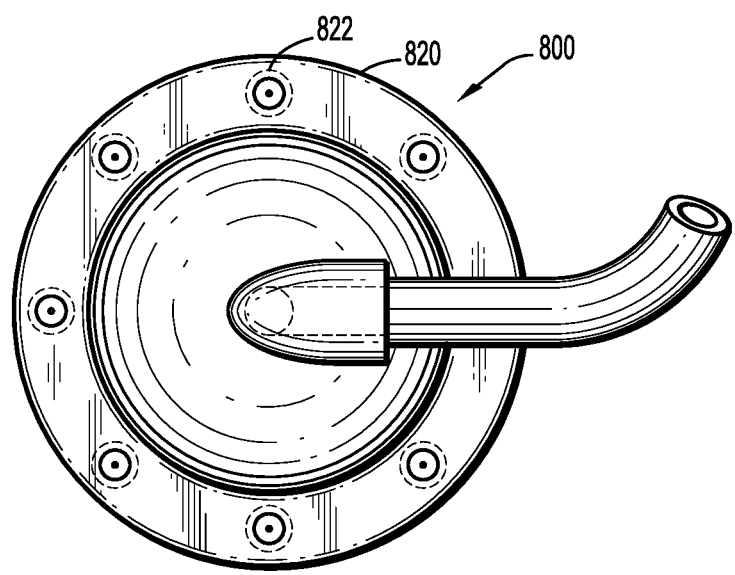

With reference to FIGS. 8A and 8B, in yet another embodiment, a wound port 800 is shown. Instead of using tubes as described above to allow a controlled or fixed leak, a number of small holes arranged in a circumference around the wound port 800 may be provided. The holes may take the form of a simple puncture 810 of a given size as shown in FIG. 8A. Alternatively, the holes 822 may be formed in a plate 820 that is radio frequency (RF) welded to the wound port 800.

Figure 9:
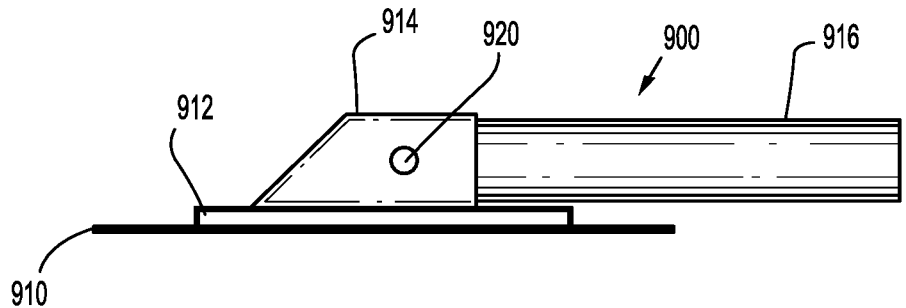
FIG. 9 depicts an alternative embodiment of the wound port in accordance with the present disclosure.

With reference to FIG. 9, in yet another embodiment, a cross section of wound port 900 is shown. Wound port 900 is operatively connected to wound dressing 910 and includes a flange 912. Flange 912 may have a circular or any polygonal shape. A body 914 is connected to the flange 912 which is fluidly connected to conduit 916. Conduit 916 leads directly or indirectly to the collection canister. Body 914 has as small orifice 920 used to provide a controlled leak into the wound site. The diameter of the orifice 920 and the pressure difference between the outside of the wound port 900 and the inside of the wound port 90 create a controllable air leak into the wound port 900 via the orifice. The small orifice 920 can be created in various ways. The orifice 920 can be integral to the port design, such as a molded in feature. It can be created via post molding micro-piercing into the port using a needle or syringe. Alternatively, assembly or insertion of a small tube that allows for communication of air from outside the wound port 900 to inside the wound port 900 can be used to create the orifice 920.

Figure 10A:
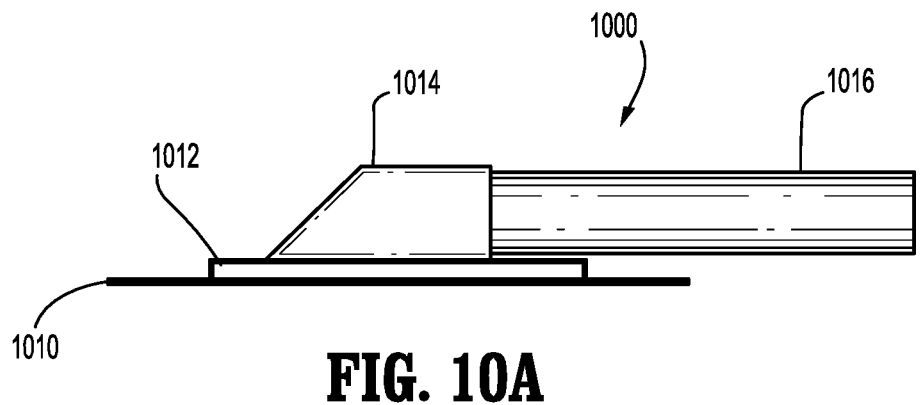
FIGS. 10A and 10B depict alternative embodiments of the wound port in accordance with the present disclosure.
Figure 10B:
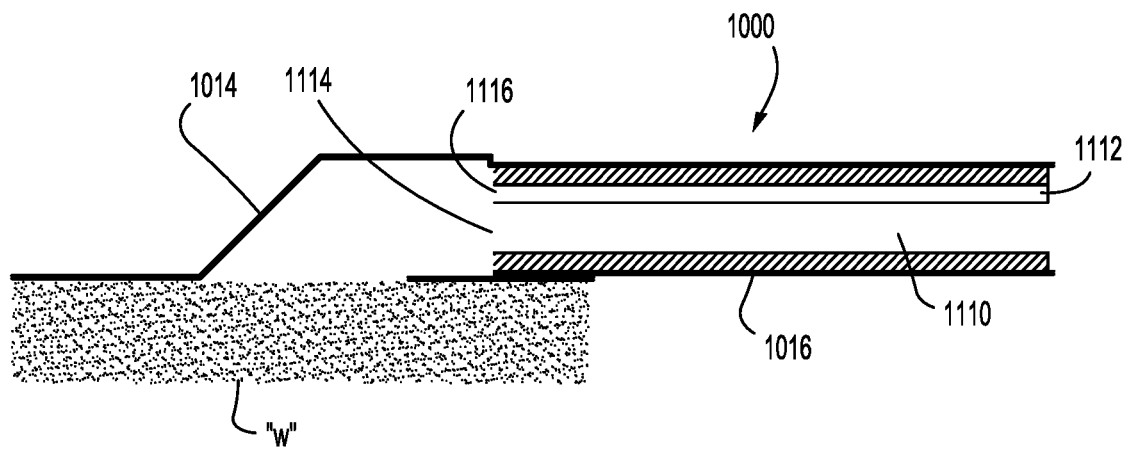

With reference to FIGS. 10A and 10B, in yet another embodiment, a wound port 1000 is shown. Wound port 1000 is operatively connected to wound dressing 1010 and includes a flange 1012. Flange 1012 may have a circular or any polygonal shape. A body 1014 is connected to the flange 1012 which is fluidly connected to conduit 1016. Conduit 1016 leads directly or indirectly to the collection canister. Conduit 1016 includes a main lumen 1110 used to provide a pathway for exudate between the wound "w" and the collection canister. A secondary lumen or vent lumen is provided in conduit 1016 to provide a controlled leak to the wound site. Exudate enters lumen 1110 at area 1114 and air exits lumen 1112 at area 1116. Secondary lumen 1112 is exposed to the ambient environment or to a source of air to provide a controlled leak in the wound port 1000. Although FIG. 10B depicts lumens 1110 and 1112 in a single conduit 1016, lumens 1110 and 1112 can be provided as separate conduits.

Figure 11A:
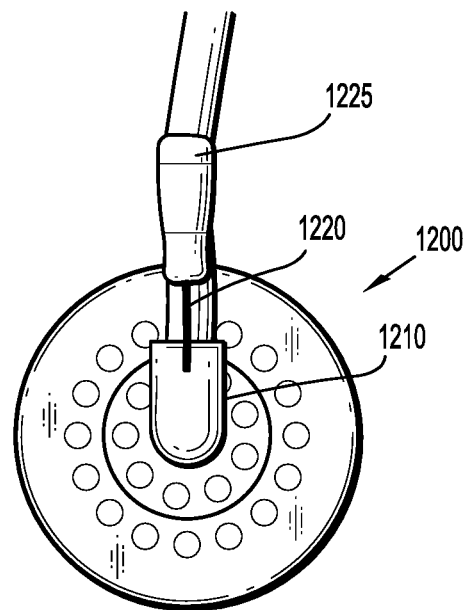
FIGS. 11A-11D depict alternative embodiments of the wound port in accordance with the present disclosure.
Figure 11B:
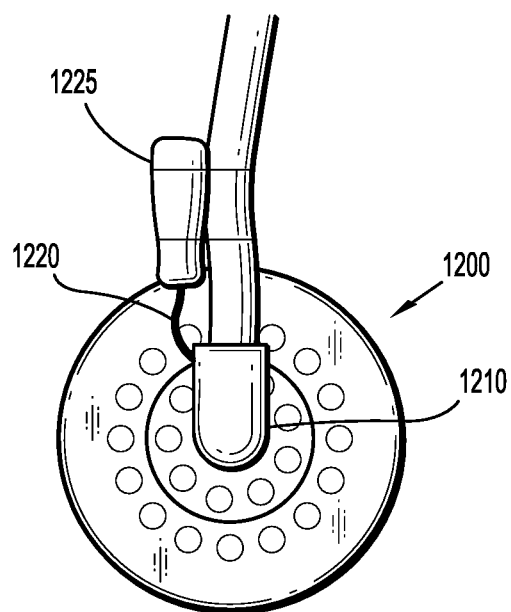
Figure 11C:
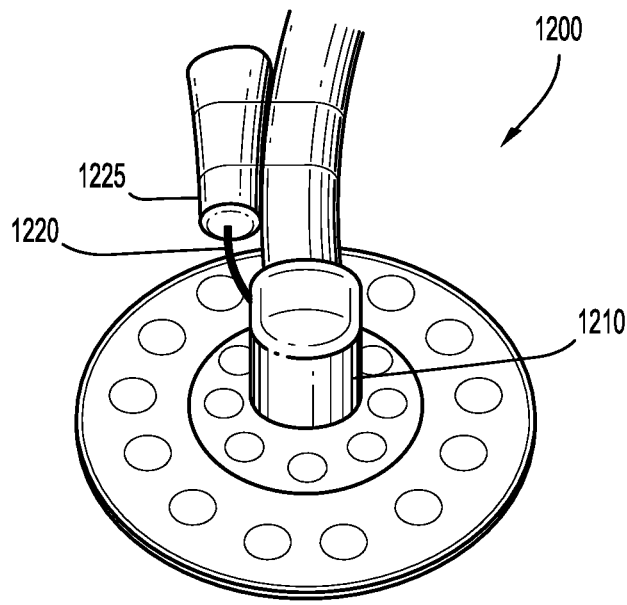
Figure 11D:
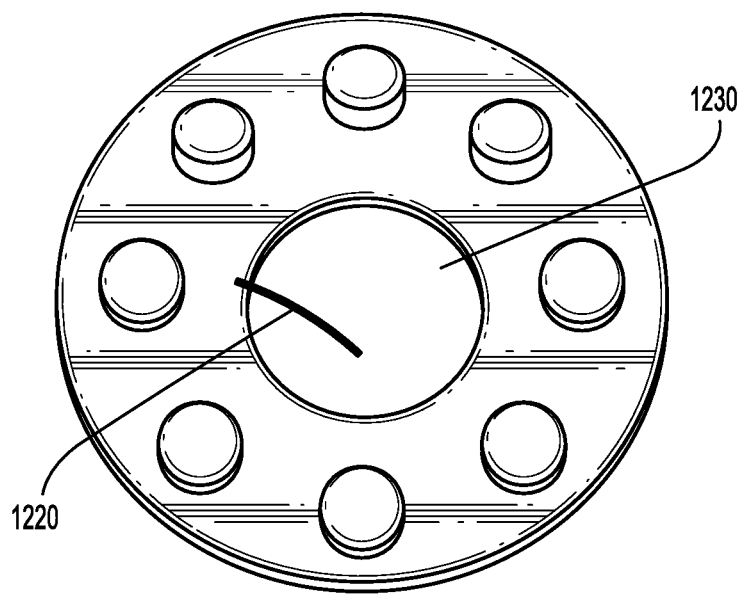

With reference to FIG. 11A, in yet another embodiment, a wound dressing 1200 is shown having a wound port 1210. Wound dressing 1200 and wound port 1210 are similar to wound dressing 12, 112, and 212 and wound port 1210 are similar to wound port 30, 130 and 230 described hereinabove. A vent conduit 1220 may be inserted into the top of wound port 1210 to provide a source of filtered air into the wound dressing 1200 through the vent conduit 1220. Vent conduit 1220 may be a stainless steel needle having a lumen extending through the needle. The end of vent conduit 1220 has filter 1225 to filter the air from the ambient atmosphere. The low flow filtered air flowing from the ambient atmosphere through the vent conduit 1220, in combination with the high flow drainage occurring through an exudate conduit, creates a sump action between the wound and a collection canister. This sump action ensures continuous flow through exudate conduit 36, thereby preventing fluid stagnation and its complications. As discussed above, the difference in size between exudate conduit and vent conduit 1220 results in capillary action that causes fluid to flow only through the larger exudate conduit. FIGS. 11B-11D depict a wound port 1210 similar to the wound port in FIG. 11A. In FIGS. 11B-11D, the vent conduit 1220 is placed on the side of the wound port 1210 rather than the top of the wound port 1210 as shown in FIG. 11A. FIG. 11D depicts the end of vent conduit 1220 being located in the wound port 1210 above an exudate orifice 1230.

Although the foregoing disclosure has been described in some detail by way of illustration and example, for purposes of clarity or understanding, it will be obvious that certain changes and modifications may be practiced within the scope of the appended claims. For example, the individual fluid and vent conduits may be substituted for by a conduit having a dual lumen. To ensure the capillary action, one lumen must be larger than the other; however, the lumens may be coaxial or parallel.

What is claimed is:

1. A system for treating a wound site with reduced pressure, the system comprising:
   a wound filler configured to be placed proximate to the wound site;
   a cover layer configured to cover the wound filler;
   a conduit comprising a first segment comprising a primary lumen and a second segment integral with the first segment comprising a secondary lumen; and
   a port, the port comprising:
      a port body having a cavity, the cavity configured to be coupled to the wound filler through an aperture in the cover layer,
   wherein:
      the port is configured to couple the primary lumen to the cavity within the port,
      the port body has a second passageway configured to couple the secondary lumen to the wound filler, the second passageway configured to fluidly isolate the secondary lumen from direct pneumatic coupling with the cavity; and
      the second passageway extends at least from the secondary lumen past a bottom surface of the port.

2. The system according to claim 1, wherein the primary lumen has a larger diameter than the secondary lumen.

3. The system according to claim 1, wherein the cavity is larger than the second passageway.

4. The system according to claim 1, comprising a reduced pressure source configured to be coupled to the primary lumen.

5. The system according to claim 1, wherein the port has a base configured to be coupled with the cover layer and extend over a larger area of the cover layer than a portion of the port adjacent to the base.

6. The system according to claim 1, wherein the second passageway comprises an elbow within the port.

7. The system according to claim 1, wherein a fluid flow path through at least the secondary lumen and the second passageway is configured to extend into the wound when the port is attached to the cover layer.

8. The system according to claim 1, wherein a fluid flow path through at least the secondary lumen and the second passageway includes a filter at an end opposite from an end that extends beyond a wound-facing surface of the port.

9. The system according to claim 1, wherein a fluid flow path through at least the secondary lumen and the second passageway includes a puncturing tip at an end that extends beyond a wound-facing surface of the port.

10. The system according to claim 1, wherein a fluid flow path through at least the secondary lumen and the second passageway comprises a valve operable to control a flow of fluid into the wound.

11. The system according to claim 10, wherein the valve is a needle valve.

12. The system according to claim 1, wherein the port is circular, and wherein a fluid flow path through at least the secondary lumen and the second passageway is placed around an interior circular portion of the port.

13. The system according to claim 1, wherein the wound filler further comprises a wound packing material configured to be disposed in the wound, and wherein a fluid flow path through at least the secondary lumen and the second passageway is configured to extend into the wound packing material when the port is attached to the cover layer.

14. The system according to claim 1, wherein a fluid flow path through at least the secondary lumen and the second passageway is configured to introduce atmospheric air under the cover layer.

15. A system for treating a wound site with reduced pressure, the system comprising:
   a wound filler configured to be placed proximate to the wound site;
   a cover layer configured to cover the wound filler;
   a conduit comprising a first segment comprising a primary lumen and a second segment integral with the first segment comprising a secondary lumen; and
   a port, the port comprising:
      a port body having a cavity, the cavity configured to be coupled to the wound filler through an aperture in the cover layer,
   wherein:
      the port is configured to couple the primary lumen to the cavity within the port,
      the port body has a second passageway configured to couple the secondary lumen to the wound filler, the second passageway configured to fluidly isolate the secondary lumen from direct pneumatic coupling with the cavity; and
      a fluid flow path through at least the secondary lumen and the second passageway is configured to extend into the wound when the port is attached to the cover layer.

16. The system according to claim 15, wherein the primary lumen has a larger diameter than the secondary lumen.

17. The system according to claim 15, comprising a reduced pressure source configured to be coupled to the primary lumen.

18. The system according to claim 15, wherein the second passageway comprises an elbow within the port.

19. The system according to claim 15, wherein the port has a base configured to be coupled with the cover layer and extend over a larger area of the cover layer than a portion of the port adjacent to the base.

20. The system according to claim 15, wherein the fluid flow path through at least the secondary lumen and the second passageway includes a filter at an end opposite from an end that extends beyond a wound-facing surface of the port.

* * * * *